US008999716B2

(12) United States Patent
Gundlach et al.

(10) Patent No.: US 8,999,716 B2
(45) Date of Patent: Apr. 7, 2015

(54) ARTIFICIAL MYCOLIC ACID MEMBRANES

(75) Inventors: Jens Gundlach, Seattle, WA (US); Ian M. Derrington, Seattle, WA (US); Kyle W. Langford, University Place, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 13/592,030

(22) Filed: Aug. 22, 2012

(65) Prior Publication Data

US 2013/0146456 A1 Jun. 13, 2013

Related U.S. Application Data

(63) Continuation of application No. PCT/US2011/025960, filed on Feb. 23, 2011.

(60) Provisional application No. 61/307,441, filed on Feb. 23, 2010, provisional application No. 61/375,707, filed on Aug. 20, 2010.

(51) Int. Cl.
*G01N 27/447* (2006.01)
*G01N 33/487* (2006.01)
*B82Y 5/00* (2011.01)

(52) U.S. Cl.
CPC ........ *G01N 27/447* (2013.01); *G01N 33/48721* (2013.01); *G01N 27/44704* (2013.01); *B82Y 5/00* (2013.01); *Y10S 977/781* (2013.01); *Y10S 977/924* (2013.01); *Y10S 977/712* (2013.01); *Y10S 977/714* (2013.01)

(58) Field of Classification Search
CPC ................. C11C 1/00–1/06; C11C 3/00–3/14; C07D 303/38–303/48
USPC .................................... 977/712–714; 436/71
See application file for complete search history.

(56) References Cited

U.S. PATENT DOCUMENTS

| 6,171,830 | B1 * | 1/2001 | Verschoor ..................... 435/134 |
| 6,406,880 | B1 | 6/2002 | Thornton |
| 2002/0052412 | A1 * | 5/2002 | Verschoor et al. ............ 514/557 |
| 2004/0063200 | A1 | 4/2004 | Chaikof |
| 2006/0008519 | A1 * | 1/2006 | Davidsen et al. ............. 424/450 |

(Continued)

FOREIGN PATENT DOCUMENTS

JP 07-248329 A 9/1995
WO 2007041621 A2 4/2007

OTHER PUBLICATIONS

Butler, T. Z., et al. "Single-molecule DNA detection with an engineered MspA protein nanopore", Proceedings of the National Academy of Science USA, vol. 105, No. 52, Dec. 30, 2008, p. 20647-20652.*

(Continued)

*Primary Examiner* — J. Christopher Ball
(74) *Attorney, Agent, or Firm* — Christensen O'Connor Johnson Kindness PLLC

(57) ABSTRACT

Provided herein are artificial membranes of mycolic acids. The membranes may be unsupported or tethered. These membranes are long lived and highly resistant to electroporation, demonstrating their general strength. The mycolic acid membranes are suitable for controlled studies of the mycobacterial outer membrane and can be used in other experiments, such as nanopore analyte translocation experiments.

19 Claims, 6 Drawing Sheets

(56) References Cited

U.S. PATENT DOCUMENTS

| | | |
|---|---|---|
| 2007/0190542 A1 | 8/2007 | Ling |
| 2007/0269843 A1 | 11/2007 | Thornton |
| 2009/0298072 A1 | 12/2009 | Ju |
| 2011/0150981 A1* | 6/2011 | Baird et al. .................. 424/450 |

OTHER PUBLICATIONS

International Search Report and Written Opinion mailed Dec. 7, 2011, issued in corresponding International Application No. PCT/US2011/025960, filed Feb. 23, 2011, 6 pages.

Rhee, M., and M.A. Burns, "Nanopore Sequencing Technology: Research Trends and Applications," Trends in Biotechnology 24(12):580-586, Dec. 2006.

International Search Report and Written Opinion mailed Nov. 28, 2011, issued in International Application No. PCT/US2011/025963, filed Feb. 23, 2011, 9 pages.

International Preliminary Report on Patentability mailed Aug. 28, 2012, issued in International Application No. PCT/US2011/025963, filed Feb. 23, 2011, 6 pages.

Notification of the First Office Action mailed Oct. 8, 2013, issued in the Chinese Application No. 201180018449.5, filed Feb. 23, 2011, 6 pages.

Notification of the First Office Action mailed Apr. 23, 2014, issued in corresponding Chinese Application No. 201180018451.2, filed Feb. 23, 2011, 7 pages.

Notification of the Third Office Action mailed Oct. 29, 2014, issued in Chinese Patent Application No. 201180018449.5, filed Feb. 23, 2011, 3 pages.

Notification of the Second Office Action mailed Dec. 3, 2014, issued in corresponding Chinese Patent Application No. 201180018451.2, filed Feb. 23, 2011, 10 pages.

* cited by examiner

ARTIFICIAL MYCOLIC ACID MEMBRANES

CROSS-REFERENCES TO RELATED APPLICATIONS

This application is a continuation of International Application No. PCT/US2011/025960, filed Feb. 23, 2011, which claims the benefit of U.S. Provisional Application Ser. No. 61/307,441, filed Feb. 23, 2010, and U.S. Provisional Application Ser. No. 61/375,707, filed Aug. 20, 2010, each of which is incorporated herein by reference in its entirety.

STATEMENT OF GOVERNMENT LICENSE RIGHTS

This invention was made with Government support under Grant Numbers R01HG005115 and 5R21HG004145 awarded by the National Institutes of Health. The Government has certain rights in the invention.

BACKGROUND

*Mycobacteria*, including *Mycobacterium tuberculosis*, have developed strains that resist contemporary multi-drug treatment regimes. With nearly two million yearly deaths caused by infections of *M. tuberculosis* and with more than 200,000 people debilitated by infections of *M. leprae* there is concerted need to understand the mechanisms of Mycobacterial resilience. Part of the persistence and lethality of these diseases is due to the impermeable *mycobacteria* cell wall. *Mycobacteria*'s unique ~8 nm thick outer cellular casing has far lower permeability to hydrophilic agents than *Escherichia coli*'s cell wall and is a key factor in the drug and environmental resistance of *mycobacteria*.

Although containing other constituents, the mycobacterial outer membrane contains 30%-40% mycolic acids. Mycolic acids contain a carboxylic acid headgroup with two hydrophobic tails of unequal length. See FIG. 1 for exemplary mycolic acids. In vivo, mycolic acids are covalently linked by the carboxylate group to peptidoglycans or trehalose sugars. The significant impermeability of the mycobacterial membranes results in the need for pathways for hydrophilic solutes. This pathway is mediated by protein pores.

In vivo studies of pore proteins in the mycobacterial cell-wall of *M. smegmatis*, a close relative of *M. tuberculosis*, led to the discovery of the outer membrane pore *M. smegmatis* porin A (MspA). In *M. smegmatis*, MspA is the most abundant protein and forms the primary pathway for hydrophilic nutrients to traverse the outer membrane. OmpATb, another protein pore, and ion transporters have been isolated in mycobacterium species but their behavior in their natural environment remains unexplored.

To investigate various properties of pores, such pores are often embedded in membranes. There is a need to develop suitable membranes for these and other experiments involving mycolic acid membranes.

SUMMARY

Provided herein is an artificial membrane comprising a mycolic acid, systems comprising such membranes, and methods of making and using such membranes. Accordingly, some embodiments provide an artificial membrane comprising a mycolic acid. Some embodiments provide an artificial membrane consisting of a plurality of mycolic acids. Some embodiments provide an artificial membrane consisting of a plurality of mycolic acids and admixtures of other lipids. Other embodiments provide an artificial membrane consisting essentially of a plurality of mycolic acids and a nanopore. Other embodiments provide an artificial membrane consisting essentially of a plurality of mycolic acids, admixtures of other lipids, and a nanopore.

Further provided is a system comprising an artificial membrane comprising a mycolic acid positioned between a first liquid conductive medium and a second liquid conductive medium. Also provided are methods comprising applying an electric field to the system.

Methods of preparing artificial unsupported mycolic membranes comprising a mycolic acid are also provided. One embodiment provides a method of making an artificial unsupported membrane comprising a mycolic acid, comprising: (a) pretreating an aperture of about 500 nm to about 500 μm in diameter with one or more coats of a mycolic acids-hexane mixture and removing the hexane to provide dry mycolic acids; (b) applying a hydrocarbon solvent to the dry mycolic acids followed by heating to promote hydrocarbon solvent incorporation to provide a mycolic acids-hydrocarbon solvent composition; (c) placing the aperture between a first liquid conductive medium and a second liquid conductive medium; (d) applying the mycolic acids-hydrocarbon solvent composition to the aperture while monitoring an ion current through the aperture until aperture resistance increases to above 1 TΩ, followed by forcing one of the liquid conductive mediums through the aperture from the trans side to eliminate ion current blockage as needed; and (e) placing an air bubble over the aperture followed by retraction of the air bubble, wherein membrane formation is indicated by the aperture resistance increasing to above 1 TΩ, and wherein bilayer membrane formation is indicated if a nanopore can form within the membrane.

DESCRIPTION OF THE DRAWINGS

The foregoing aspects and many of the attendant advantages of this invention will become more readily appreciated as the same become better understood by reference to the following detailed description, when taken in conjunction with the accompanying drawings.

DETAILED DESCRIPTION

Figure 1:
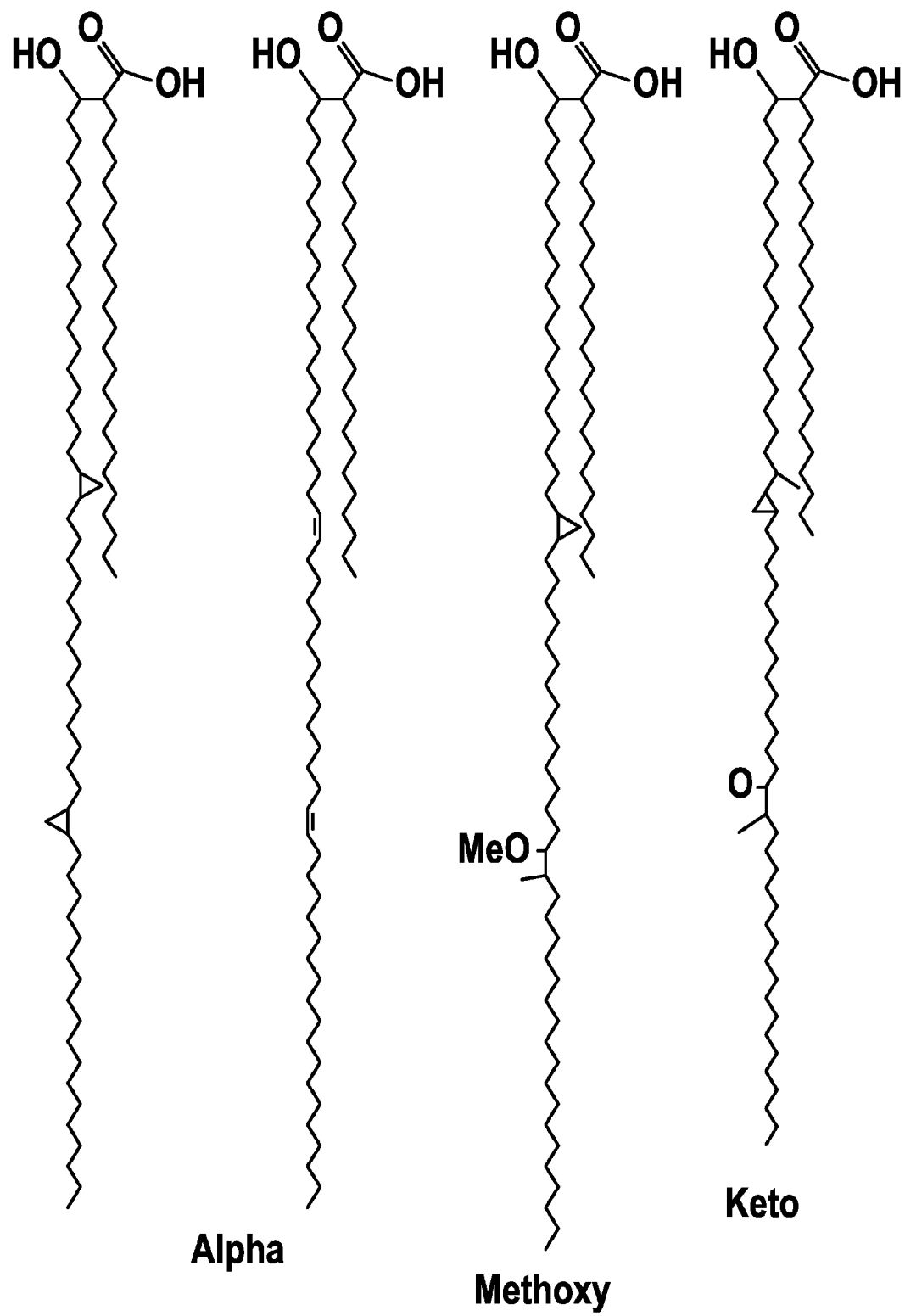
FIG. 1 shows the chemical structures of exemplary mycolic acids present in mycobacterial outer membranes. See Annu Rev Biochem 64:29 (1995).

Provided herein are artificial membranes comprising a mycolic acid. These membranes are long lived and highly resistant to electroporation, demonstrating their general strength. The mycolic acid membranes are suitable for, e.g., controlled studies of the mycobacterial outer membrane and can be used for nanopore analyte translocation experiments as well as other applications described below.

Accordingly, provided herein is an artificial membrane comprising a mycolic acid. In any embodiment herein, the membrane may be unsupported or tethered. A mycolic acid may be further defined as a modified mycolic acid. A modified mycolic acid may be a crosslinked mycolic acid. A mycolic acid may be further defined as not a modified mycolic acid. In some embodiments, a membrane has average thickness ranging from about 5 to about 22 nm. In some embodiments, the average thickness is about, at most about, or at least about 5, 6, 7, 8, 9, 10, 11, 12, 13, 14, 15, 16, 17, 18, 19, 20, 21, or 22 nm or more, or any range derivable therein. Methods of measuring thickness of membranes are well-known in the art and an example is provide in the Examples below.

In some embodiments, a membrane has an average rupture voltage of about 2.0 V when voltage applied across the membrane is ramped at about 100 mV/s in the presence of a 1.0 M KCl solution prepared with deionized water, buffered to pH 8.0±0.05 with 10 mM HEPES. An example of determining an average rupture voltage is provided herein. In some embodiments, a membrane has an ability to withstand voltages greater than 1 V for greater than several hours in the presence of a 1.0 M KCl solution prepared with deionized water, buffered to pH 8.0±0.05 with 10 mM HEPES. In some embodiments, a membrane has an ability to withstand voltages greater than 1 V for at least about 2, 3, 4, or 5 or more hours, or any range derivable therein, in the presence of a 1.0 M KCl solution prepared with deionized water, buffered to pH 8.0±0.05 with 10 mM HEPES. In some embodiments, a membrane has a resistance to rupture when buffers on cis or trans sides are removed. A membrane may be formed and reformed when exposed to pH 2 to pH 9 buffer presented to its cis side. In some embodiments, a membrane may be formed and reformed at temperatures exceeding 55° C.

An artificial membrane comprising a mycolic acid may further comprise a variety of substances. In some embodiments, a membrane further comprises a nanopore. In some embodiments, a membrane further comprises a plurality of nanopores. Optionally, the nanopore is a protein pore. In some embodiments, the protein pore is further defined as α-hemolysin or a variant thereof, a *Mycobacterium smegmatis* porin (Msp) porin, or OmpATb. In some embodiments, the protein pore is further defined as α-hemolysin or a variant thereof. In some embodiments, the nanopore is a mutant MspA porin. In some embodiments, amino acids at positions 90, 91, and 93 of a mutant MspA porin are each substituted with asparagine. Any membrane may further comprise a drug. In some embodiments, the drug is an antibacterial drug for the treatment of tuberculosis. In some embodiments, a membrane further comprises an enzyme, a molecular motor, a nanoparticle, an optical bead, a magnetic bead, or light.

In some embodiments, the membrane is further defined as a bilayer membrane.

Also provided is an artificial membrane consisting of a plurality of mycolic acids. Also provided is an artificial membrane consisting of a plurality of mycolic acids and admixtures of other lipids.

Some embodiments provide an artificial membrane consisting essentially of a plurality of mycolic acids and a nanopore. Materials or steps that do not materially affect the basic and novel characteristics of such embodiments include those that do not affect the lipid nature of the mycolic acid or prevent formation of the membrane.

Some embodiments provide an artificial membrane consisting essentially of a plurality of mycolic acids, admixtures of other lipids, and a nanopore. Materials or steps that do not materially affect the basic and novel characteristics of such embodiments include those that do not affect the lipid nature of the mycolic acid or other lipids or that prevent formation of the membrane.

In some embodiments, a system is provided comprising an artificial membrane comprising a mycolic acid positioned between a first liquid conductive medium and a second liquid conductive medium. At least one liquid conductive medium may comprise an analyte, such as a nucleic acid or a protein. In some embodiments, the membrane further comprises a nanopore. The nanopore may be further defined as a protein that forms a tunnel upon insertion into the membrane. In some embodiments, the protein is a mutant *M. smegmatis* porin A porin (mutant MspA porin). In some embodiments, amino acids at positions 90, 91, and 93 of the mutant MspA porin are each substituted with asparagine. In some embodiments, at least one liquid conductive medium comprises an analyte, wherein membrane further comprises a nanopore, and wherein the system is operative to detect a property of the analyte. A property of an analyte may be an electrical, chemical, or physical property. In some embodiments, at least one liquid conductive medium comprises an analyte, wherein the membrane further comprises a protein pore having a tunnel, and wherein the system is operative to electrophoretically translocate the analyte through the tunnel. A system may further comprise a patch-clamp amplifier, a data acquisition device, one or more temperature regulating devices in communication with the first liquid conductive medium or the second liquid conductive medium, or any combination thereof.

Methods may comprise applying an electric field to any system described herein. Some methods further comprise detecting an analyte in the system in a method comprising measuring an ion current as the analyte interacts with an opening of a nanopore to provide a current pattern, wherein the appearance of a blockade in the current pattern indicates the presence of the analyte. In some embodiments, applying an electric field is sufficient to cause the analyte to electrophoretically translocate through the opening. A method may further comprise identifying the analyte. Identifying the analyte may comprise comparing the current pattern to a known current pattern of a known analyte.

Also provided is a method of making an artificial unsupported membrane comprising a mycolic acid, comprising: (a) pretreating an aperture of about 500 nm to about 500 μm in diameter with one or more coats of a mycolic acids-hexane mixture and removing the hexane to provide dry mycolic acids; (b) applying a hydrocarbon solvent to the dry mycolic acids followed by heating to promote hydrocarbon solvent incorporation to provide a mycolic acids-hydrocarbon solvent composition; (c) placing the aperture between a first liquid conductive medium and a second liquid conductive medium; (d) applying the mycolic acids-hydrocarbon solvent composition to the aperture while monitoring an ion current through the aperture until aperture resistance increases to above 1 TΩ, followed by forcing one of the liquid conductive mediums through the aperture from the trans side to eliminate ion current blockage as needed; and (e) placing an air bubble over the aperture followed by retraction of the air bubble, wherein membrane formation is indicated by the aperture resistance increasing to above 1 TΩ, and wherein bilayer membrane formation is indicated if a nanopore can form within the membrane. The hydrocarbon solvent may be hexadecane or hexadecene or any other hydrocarbon solvent that may be incorporated into the membrane. The type of hydrocarbon solvent employed depends on the temperature at which one wants to prepare the membrane.

Mycolic acids are high molecular weight α-branched, β-hydroxy fatty acids that are components of the cell envelopes of all *Mycobacteria*. Mycolic acids contain a carboxylic acid headgroup with two hydrophobic tails of unequal length. Mycolic acids have the basic structure $R^2CH(OH)CHR^1COOH$, where $R_1$ is a $C_{20}$-$C_{24}$ linear alkane and $R^2$ is a more complex structure of 30-60 carbon atoms that may contain various numbers of carbon-carbon double bonds, cyclopropane rings, methyl branches or oxygen functions such as carbonyl, carboxylic acid, and methoxy groups. The structure of mycolic acids varies by families and species.

In the mycobacterial cell envelope, mycolic acids are present as free lipids, such as trehalose dimycolate (TDM) or cord factor and trehalose monomycolate (TMM). They may also be esterified to the terminal penta-arabinofuranosyl units of arabinogalactan, a peptidoglycan-linked polysaccharide. Herein, a mycolic acid may be further defined as any of these variants. In some embodiments, a mycolic acid is further defined as a trehalose-modified mycolic acid that may be naturally-occurring or synthetic, which are known in the art. See, e.g., U.S. Pat. Nos. 4,307,229, 4,720,456, 5,006,514, and 5,049,664, each of which is incorporated herein by reference in its entirety. The presence of such long-chain fatty acids is largely responsible for the high hydrophobicity and very low permeability of the mycobacterial cell envelope. Mycolic acids have been reported in bacterial species other than *Mycobacterium*, e.g., *Corynebacterium* and *Nocardia*. Consequently, three major categories of mycolic acids are distinguished (The Merck Index, 1989), namely:

i) corynomycolic acids ($C_{28}$-$C_{40}$ acyl chain length)
ii) nocardomycolic acids ($C_{40}$-$C_{60}$ acyl chain length) and
iii) mycobacterial mycolic acids ($C_{60}$-$C_{90}$ acyl chain length).

A detailed description of the structures of MA, motifs, and variations is provided in Prog Lipid Res 37:143 (1998). MA may be purchased, such as from Sigma Aldrich, or prepared as is known in the art. See, e.g., U.S. Pat. No. 6,171,830, incorporated herein by reference in its entirety.

The definition of mycolic acids also includes modified mycolic acids. Accordingly, membranes may comprise one or more modified mycolic acids. For example, mycolic acids may be modified by crosslinking mycolic acids. Mycolic acid membranes may be made to be more gel-like and stable by end-group polymerization or by crosslinking of internal groups of mycolic acids. Methods of crosslinking similar to methods of crosslinking dipalmitoylphosphatidylcholine (DPhPC) or other lipids, as is known in the art, may be employed to prepare modified mycolic acids. See, e.g., A. Singh and J. M. Schnur, Polymerizable Phospholipids in Phospholipids Handbook, C. Cevc, ed., Marcel Dekker Inc., NY, pp 233-287 (1993).

A membrane as described herein may comprise one or more types of mycolic acids (that is, mixtures of mycolic acids). In some embodiments, a membrane comprises about, at least about, or at most about 1%, 2%, 5%, 10%, 15%, 20%, 25%, 30%, 35%, 40%, 45%, 50%, 55%, 60%, 65%, 70%, 75%, 80%, 85%, 90%, 95%, 98%, 99%, or more mycolic acids, or any range derivable therein. In some embodiments, a membrane comprises 100% mycolic acids. In some embodiments, mycolic acids are derived from *M. tuberculosis*.

By "artificial," it is meant that the membranes are not naturally-occurring but are instead man-made.

The ability to construct artificial membranes comprising a mycolic acid may provide a new tool to examine the arrangement and configuration of the mycolic acid lipids in a membrane. Furthermore, the membranes may permit the controlled examination of drugs and chemicals through outer membrane pores found in mycobacterial outer membranes, such as MspA and possibly Rv1689. Such examination may help to improve treatment of mycobacterial infections.

Beyond research in *mycobacteria*, the membranes may provide a building block for nanotechnological (e.g., bio-nanotechnological) applications that rely on the stability of lipid membranes. These include next-generation nucleic acid sequencing and nanopore force spectroscopy. In this regard, this application incorporates by reference in its entirety the international application entitled, "Analyte Sequencing with Nanopores," by Jens H. Gundlach, Ian M. Derrington, and Marcus D. Collins filed in the U.S. Receiving Office on Feb. 23, 2011. This application also incorporates by reference U.S. Provisional Application Ser. No. 61/098,938 and its related PCT application, WO 2010/034018, titled "Msp Nanopores and Related Methods," each in its entirety. Methods disclosed in these applications may be employed with the mycolic acid membranes disclosed herein.

Further, several types of observable signals are being explored as readout mechanisms in nanopore sequencing and analyte detection. The originally proposed, most straightforward, and most explored readout method relies on an ionic "blockade current" or "copassing current" uniquely determined by the identity of a nucleotide or other analyte occupying the narrowest constriction in the pore. This method is referred to as "blockade current nanopore sequencing," or BCNS. Blockade current detection and characterization of nucleic acids has been demonstrated in the protein pore α-hemolysin, mutant MspA porins, and solid-state nanopores. Blockade current detection and characterization has been shown to provide a host of information about the structure of DNA passing through, or held in, a nanopore in various contexts. Similar experiments may be performed with such nanopores embedded in mycolic acid membranes described herein.

In general, a "blockade" is evidenced by a change in ion current that is clearly distinguishable from noise fluctuations and is usually associated with the presence of an analyte molecule at the pore's central opening. The strength of the blockade will depend on the type of analyte that is present. More particularly, a "blockade" refers to an interval where the ionic current drops below a threshold of about 5-100% of the unblocked current level, remains there for at least 1.0 μs, and returns spontaneously to the unblocked level. For example, the ionic current may drop below a threshold of about, at least about, or at most about 5%, 10%, 15%, 20%, 25%, 30%, 35%, 40%, 45%, 50%, 55%, 60%, 65%, 70%, 75%, 80%, 85%, 90%, 95%, or 100%, or any range derivable therein. Blockades are rejected if the unblocked signal directly preceding or following it has an average current that deviates from the typical unblocked level by more than twice the rms noise of the unblocked signal. "Deep blockades" are identified as intervals where the ionic current drops <50% of the unblocked level. Intervals where the current remains between 80% and 50% of the unblocked level are identified as "partial blockades."

In some embodiments, the ion current amplitude through the pore may be converted to a fluorescent optical system as is well known in the art. See, e.g., J Amer Chem Soc 13:1652 (2009).

Artificial mycolic acid membranes may also be used to screen for drugs that have improved permeability, to understand membrane impermeability to drugs, and to evaluate known and unknown drug efflux pumps in the membrane (see Trends Microbiol 18:109 (2010)). The membranes could also be used to evaluate membrane proteins such as Msp porins (e.g., MspA and mutant MspA) and OmpATb as drug targets.

Also contemplated is method whereby poration of a mycolic acid membrane is observed after a drug has been presented to the trans or cis side of the membrane. Perforation of the membrane may be observed by monitoring an ion current or by employing fluorescent particles, or by observing the drug at the other side of the membrane. Also contemplated is a system adapted to execute such a method.

As used herein, an "unsupported membrane" is a membrane spanning the opening of an aperture with no support on either side along the surface of the membrane. The membrane has liquid, gas, or vacuum on either or both sides, but is not in contact with a solid (substrate) on either side.

As used herein, a "tethered membrane" is a membrane in which the headgroups of mycolic acids are attached, or tethered, to a substrate (e.g., plastic, glass, chip, bead). Methods of attaching lipids to substrates to form tethered membranes are well-known in the art through chemical modification of headgroups, and such methods may be used to similarly modify and attach headgroups of mycolic acids.

A "nanopore" refers to a pore having an opening with a diameter at its most narrow point of about 0.3 nm to about 2 nm. For example, a nanopore may be a solid-state nanopore, a graphene nanopore, an elastomer nanopore, or may be a naturally-occurring or recombinant protein that forms a tunnel upon insertion into a bilayer, thin film, membrane, or solid-state aperture, also referred to as a protein pore or protein nanopore herein (e.g., a transmembrane pore). If the protein inserts into the membrane, then the protein is a tunnel-forming protein. Methods of determining whether a protein is a tunnel-forming protein are well-known in the art. For example, one may determine if an Msp porin forms a tunnel by determining whether the protein inserts into a bilayer, such as described in U.S. Provisional Application Ser. No. 61/098,938 and its related PCT application, WO 2010/034018, each of which is incorporated herein by reference in its entirety, and Proc Natl Acad Sci 105:20647 (2008). Typically, tunnel formation is detected by observing a discrete change in conductivity. See, e.g., Mol Microbiol 33:933 (1999). An opening is typically in liquid or gas communication with the cis and trans sides of the nanopore. A nanopore may comprise a solid state material, such as silicon nitride, modified silicon nitride, silicon, silicon oxide, or graphene, or a combination there of (e.g., a nanopore may be prepared by making first a SiN aperture, putting a sheet of graphene over it, and then making a nanopore in the graphene). Non-limiting examples of protein nanopores (also called protein pores) include α-hemolysin and variants thereof, a *Mycobacterium smegmatis* porin (Msp) porin, and OmpATb.

A "liquid medium" includes aqueous, organic-aqueous, and organic-only liquid media. Organic media include, e.g., methanol, ethanol, dimethylsulfoxide, and mixtures thereof. Liquids employable in methods described herein are well-known in the art. Descriptions and examples of such media, including conductive liquid media, are provided in U.S. Pat. No. 7,189,503, for example, which is incorporated herein by reference in its entirety. Salts, detergents, or buffers may be added to such media. Such agents may be employed to alter pH or ionic strength of the liquid medium. Viscosity-altering substances, such as glycerol or various polymers (e.g., polyvinylpyrrolidone, polyethylene glycol, polyvinyl alcohol, cellulose polymers), and mixtures thereof, may be included in liquid media.

The first and second liquid media employed in any embodiment may be the same or different, and either one or both may comprise one or more of a salt, a detergent, or a buffer. Optionally, at least one liquid medium is conductive. Optionally, at least one liquid medium is not conductive. The liquid media may comprise any analyte described herein.

In any embodiment herein, an analyte may be a nucleotide, a nucleic acid, an amino acid, a peptide, a protein, a polymer, a drug, an ion, a pollutant, a nanoscopic object, or a biological warfare agent. Optionally, an analyte is a polymer, such as a protein, a peptide, or a nucleic acid. Optionally, the polymer is a nucleic acid. A nucleic acid may be ssDNA, dsDNA, RNA, or a combination thereof. Any analyte described herein may comprise an optical bead or a magnetic bead.

As used herein, a "drug" refers to any substance that may alter a biological process of a subject. Drugs may be designed or used for or in the diagnosis, treatment, or prevention of a disease, disorder, syndrome, or other health affliction of a subject. Drugs may be recreational in nature, that is, used simply to alter a biological process and not used for or in the diagnosis, treatment, or prevention of a disease, disorder, syndrome, or other health affliction of a subject. Biologics, which refer to substances produced by biological mechanisms involving recombinant DNA technology, are also encompassed by the term "drug." Drugs include, for example, antibacterials, antiinflammatories, anticoagulants, antivirals, antihypertensives, antidepressants, antimicrobials, analgesics, anesthetics, beta-blockers, bisphosphonates, chemotherapeutics, contrast agents, fertility medications, hallucinogens, hormones, narcotics, opiates, sedatives, statins, steroids, and vasodilators. Non-limiting examples of drugs may also be found in the Merck Index. Antibacterial drugs used in the treatment of tuberculosis, for example, include isoniazid, rifampicin, pyrazinamide, and ethambutol.

As used herein, a "polymer" refers to a molecule that comprises two or more linear units (also known as a "mers"), where each unit may be the same or different. Non-limiting examples of polymers include nucleic acids, peptides, and proteins, as well as a variety of hydrocarbon polymers (e.g., polyethylene, polystyrene) and functionalized hydrocarbon polymers, wherein the backbone of the polymer comprises a carbon chain (e.g., polyvinyl chloride, polymethacrylates). Polymers include copolymers, block copolymers, and branched polymers such as star polymers and dendrimers.

As used herein, a "biological warfare agent" refers to any organism or any naturally occurring, bioengineered, or synthesized component of any such microorganism capable of causing death or disease in plants or animals (including humans) or degradation of food or water supplies, or degradation of the environment. Non-limiting examples include Ebola viruses, Marburg virus, *Bacillus anthracis* and *Clostridium botulinum*, *Variola major*, *Variola minor*, anthrax, and ricin.

As used herein, a "pollutant" refers to a material that pollutes air, water, or soil. Non-limiting examples of pollutants include fertilizers, pesticides, insecticides, detergents, petroleum hydrocarbons, smoke, and heavy metal-containing substances, such as those containing zinc, copper, or mercury (e.g., methylmercury).

As used herein, an "amino acid" refers to any of the 20 naturally occurring amino acids found in proteins, D-stereoisomers of the naturally occurring amino acids (e.g., D-threonine), unnatural amino acids, and chemically modified amino acids. Each of these types of amino acids is not mutually exclusive. α-Amino acids comprise a carbon atom to which is bonded an amino group, a carboxyl group, a hydrogen atom, and a distinctive group referred to as a "side chain." The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), arylalkyl (e.g., as in phenylalanine and tryptophan), substituted arylalkyl (e.g., as in tyrosine), and heteroarylalkyl (e.g., as in histidine).

The following abbreviations are used for the 20 naturally occurring amino acids: alanine (Ala; A), asparagine (Asn; N), aspartic acid (Asp; D), arginine (Arg; R), cysteine (Cys; C), glutamic acid (Glu; E), glutamine (Gln; Q), glycine (Gly; G), histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

Unnatural amino acids (that is, those that are not naturally found in proteins) are also known in the art, as set forth in, for example, Mol Cell Biol 9:2574 (1989); J Amer Chem Soc 112:4011-4030 (1990); J Amer Chem Soc 56:1280-1283 (1991); J Amer Chem Soc 113:9276-9286 (1991); and all references cited therein. β- and γ-Amino acids are known in the art and are also contemplated herein as unnatural amino acids. The following table shows non-limiting examples of unnatural amino acids that are contemplated herein.

TABLE 1

Exemplary Unnatural Amino Acids

| Abbr. | Amino Acid |
| --- | --- |
| Aad | 2-Aminoadipic acid |
| Baad | 3-Aminoadipic acid |
| Bala | β-alanine, β-Amino-propionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| Baib | 3-Aminoisobutyric acid |
| Apm | 2-Aminopimelic acid |
| Dbu | 2,4-Diaminobutyric acid |
| Des | Desmosine |
| Dpm | 2,2'-Diaminopimelic acid |
| Dpr | 2,3-Diaminopropionic acid |
| EtGly | N-Ethylglycine |
| EtAsn | N-Ethylasparagine |
| Hyl | Hydroxylysine |
| AHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| Nva | Norvaline |
| Nle | Norleucine |
| Orn | Ornithine |

As used herein, a "chemically modified amino acid" refers to an amino acid whose side chain has been chemically modified. For example, a side chain may be modified to comprise a signaling moiety, such as a fluorophore or a radiolabel. A side chain may be modified to comprise a new functional group, such as a thiol, carboxylic acid, or amino group. Post-translationally modified amino acids are also included in the definition of chemically modified amino acids.

As used herein, a "peptide" refers to two or more amino acids joined together by an amide bond (that is, a "peptide bond"). Peptides comprise up to or include 50 amino acids. Peptides may be linear or cyclic. Peptides may be α, β, γ, δ, or higher, or mixed. Peptides may comprise any mixture of amino acids as defined herein, such as comprising any combination of D, L, α, β, γ, δ, or higher amino acids.

As used herein, a "protein" refers to an amino acid sequence having 51 or more amino acids.

The term "nucleic acid" refers to a deoxyribonucleotide or ribonucleotide polymer in either single- or double-stranded form, and unless otherwise limited, encompasses known analogs of natural nucleotides that hybridize to nucleic acids in manner similar to naturally occurring nucleotides, such as peptide nucleic acids (PNAs) and phosphorothioate DNA. Unless otherwise indicated, a particular nucleic acid sequence includes the complementary sequence thereof. Nucleotides include, but are not limited to, ATP, dATP, CTP, dCTP, GTP, dGTP, UTP, TTP, dUTP, 5-methyl-CTP, 5-methyl-dCTP, ITP, dITP, 2-amino-adenosine-TP, 2-amino-deoxyadenosine-TP, 2-thiothymidine triphosphate, pyrrolo-pyrimidine triphosphate, and 2-thiocytidine, as well as the alphathiotriphosphates for all of the above, and 2'-O-methyl-ribonucleotide triphosphates for all the above bases. Modified bases include, but are not limited to, 5-Br-UTP, 5-Br-dUTP, 5-F-UTP, 5-F-dUTP, 5-propynyl dCTP, and 5-propynyl-dUTP.

"Molecular motors" are well-known in the art and refer to a molecule (e.g., an enzyme) that physically interacts with an analyte, such as a polymer (e.g., a polynucleotide), and is capable of physically moving the analyte with respect to a fixed location, such as the opening of a nanopore (e.g., a tunnel of an Msp porin). Although not intending to be bound by theory, molecular motors utilize chemical energy to generate mechanical force. In some embodiments, a molecular motor may interact with each unit (or "mer") of a polymer in a sequential manner. Non-limiting examples of molecular motors include DNA polymerases, RNA polymerases, helicases, ribosomes, and exonucleases. Non-enzymatic motors are also known, such as virus motors that pack DNA. See Nature 413:748 (2001). A variety of molecular motors and desirable properties of such motors are described in U.S. Pat. No. 7,238,485, which is incorporated herein by reference in its entirety. A molecular motor may be disposed on the cis side or the trans side of a membrane and may optionally be immobilized, such as described by the '485 patent. Methods of incorporating a molecular motor into a nanopore may be performed using, e.g., methods described in the '485 patent. Systems and apparatuses described in the '485 patent may be employed with respect to a membrane comprising a nanopore described herein as well. Molecular motors are also discussed in, e.g., J Amer Chem Soc 130:818 (2008); Nature Nanotech 2:718 (2007); and ACS Nano 3:1457 (2009). Molecular motors as described in WO 2010/034018, incorporated herein by reference in its entirety, may also be employed in the context of nanopores and membranes described herein.

Beads that may be employed include magnetic beads and optical beads. For example, one may use streptavidin-coated magnetic beads to apply an opposing force to the electrostatic forces that pull DNA through an opening of a nanopore. In this latter technique a magnetic bead is attached to biotinylated DNA, and a force comparable to the electrostatic driving force (~10 pN) would be applied using a strong magnetic field gradient. See Biophys J 82:3314 (2002). In this way, the blockade-current readout would be unaffected, but the forces on the DNA could be independently controlled. Tens or hundreds of complete, independent reads of each DNA could then be correlated and assembled to reconstruct an accurate DNA sequence. In some embodiments, beads may be used to visualize the position of the membrane or to indicate that the membrane has ruptured. The latter is useful in cases where it is not useful or possible to measure an ion current.

As used herein, a "nanoparticle" refers to a particle having one or more dimensions of the order of 100 nm or less. A "nanoscopic object," which is an object that is smaller than 100 nm in two of its dimensions.

As used herein, the "cis side of a membrane" refers to the side of a membrane in which any analyte is placed, where the analyte is optionally translocated. If no analyte is examined, the side of the membrane that is accessible via perfusion is considered the cis side of the membrane. If both sides of the membrane are equally accessible via perfusion, then the cis side may be defined by the operator.

As used herein, the "trans side of a membrane" refers to the side of a membrane opposite to the cis side of the membrane.

Mycolic acid membranes may comprise lipids other than a mycolic acid. Lipids are a class of molecules known in the art and contain a hydrophobic tail and a hydrophilic headgroup. See, e.g., U.S. Pat. No. 7,514,267, incorporated herein by reference in its entirety. In some embodiments, a lipid is a saturated or unsaturated fatty acid ranging from 3 to 28 carbons in chain length and with 0 to 6 unsaturated bonds. Lipids may have two hydrocarbon chains, typically acyl chains, and a headgroup, either polar or nonpolar. There are a variety of synthetic and naturally-occurring lipids, including the phospholipids, such as phosphatidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation.

Phospholipids that may be comprised in a mycolic acid membrane include native or synthetic phospholipids. Non-limiting examples include phosphatidylcholine (PC), phosphatidyl ethanolamine (PE), phosphatidylinositol (PI), phosphatidyl glycerol (PG), phosphatidic acid (PA), phosphatidyl serine (PS), and sphingomyelin (SM). The fatty acyl chains in the phospholipids are generally at least about 7 carbon atoms in length, typically 12-20 carbons in length, and may be entirely saturated or partially unsaturated. Further examples of phospholipids include phosphatidylcholines, such as dipalmitoyl phosphatidylcholine (DPPC or DPhPC), dilauryl phosphatidylcholine (DLPC)C12:0, dimyristoyl phosphatidylcholine (DMPC)C14:0, distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dip almitoleoyl phosphatidylcholine (C16:1), linoleoyl phosphatidylcholine (C18:2), dipalmitoyl phosphatidylethanolamine, dioleoylphosphatidylethanolamine (DOPE), dioleoyl phosphatidylglycerol (DOPG), palmitoyloleoyl phosphatidylglycerol (POPG), distearoylphosphatidylserine (DSPS) soybean lecithin, egg yolk lecithin, sphingomyelin, phosphatidylserines, phosphatidylglycerols, phosphatidyl inositols, diphosphatidyl glycerol, phosphatidylethanolamine, and phosphatidic acids.

Other lipids that may be used include 1,2-diacyl-sn-glycero-3-[phospho-rac-(1-glycerol)], 1,2-diacyl-sn-glycero-3-[phospho-L-serine], 1,2-diacyl-sn-glycero-3-phosphocholine, 1,2-diacyl-sn-glycero-3-phosphate, and 1,2-diacyl-sn-glycero-3-phosphoethanolamine where the diacyl groups may be symmetrical or asymmetrical and contain either saturated or unsaturated fatty acids of various types ranging from 3 to 28 carbons in chain length and with up to 6 unsaturated bonds. Further lipids include egg phosphatidyl choline (EPC), 1,2-dimyristoyl-sn-glycero-3-phosphocholine (DMPC), and 1,2-dimyristoyl-sn-glycero-3-[phospho-rac-(1-glycerol)].

In some embodiments, non-phospholipids, neutral lipids, glycolipids, cholesterol, sterols, steroids, and the like may be included in the membranes. In some embodiments, anionic lipids are used. Examples of anionic lipids include phosphatidic acid (PA), phosphatidylserine (PS), and phosphatidylglycerol (PG), phosphatidylcholine (PC), 1,2-dimyristoyl-sn-glycero-3-[phospho-rac-(1-glycerol)] (DMPG). Cationic lipids may also be used, in some embodiments. Such cationic lipids typically have a lipophilic moiety, such as a sterol, an acyl or diacyl chain, and where the lipid has an overall net positive charge. The headgroup of the lipid may carry a positive charge. Exemplary cationic lipids include 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy) propyl]-N,N,N-trimethylammonium chloride (DOTMA); 3 [N—(N',N'-dimethylaminoethane) carbamoly]cholesterol (DC-Chol); and dimethyldioctadecylammonium (DDAB). A lipid may also be a neutral lipid, such as dioleoylphosphatidyl ethanolamine (DOPE) or an amphipathic lipid, such as a phospholipid, derivatized with a cationic lipid, such as polylysine or other polyamine lipids.

In some embodiments, a lipid is selected to achieve a specified degree of fluidity or rigidity of a membrane, to control the stability of the membrane, or to control the rate of release of the entrapped agent (e.g., analyte) within the membrane. For example, saturated lipids may contribute to greater membrane rigidity in the lipid bilayer. Other lipid components, such as cholesterol, are also known to contribute to membrane rigidity in lipid bilayer structures.

As used herein, "translocation" and grammatical variants means to enter one side of an opening of a nanopore and move to and out of the other side of the opening. It is specifically contemplated that any embodiment herein comprising translocation may refer to electrophoretic translocation or non-electrophoretic translocation, unless specifically noted. An electric field may move an analyte such that it interacts with the opening. By "interacts," it is meant that the analyte moves into and, optionally, through the opening, where "through the opening" (or "translocates") means to enter one side of the opening and move to and out of the other side of the opening. Optionally, methods that do not employ electrophoretic translocation are contemplated, such as physical pressure or magnetic pressure when magnetic beads are employed.

A "*Mycobacterium smegmatis* porin (Msp)" or "Msp porin" refers to a multimer complex comprised of two or more Msp monomers. An Msp monomer is encoded by a gene in *M. smegmatis*. *M. smegmatis* has four identified Msp genes, denoted MspA, MspB, MspC, and MspD. An Msp porin can, for example, be comprised of wild-type MspA monomers, mutant MspA monomers, wild-type MspA paralog or homolog monomers, or mutant MspA paralog or homolog monomers. Optionally, an Msp porin is a single-chain Msp porin or is a multimer of several single-chain Msp porins. A single-chain Msp porin can, for example comprise a multimer formed by two or more Msp monomers (e.g., eight monomers) connected by one or more amino acid linker peptides. A partial single chain Msp porin refers to a single-chain multimer complex that must dimerize, trimerize, or the like to form a porin. A full single-chain Msp porin refers to a single-chain multimer complex that forms a porin without the need to dimerize, trimerize or the like to form a porin. Msp porins are known in the art as are methods of making mutant Msp porins. International application WO 2010/034018, incorporated herein by reference in its entirety, describes many of these porins and methods of making these porins.

A "vestibule" refers to the cone-shaped portion of the interior of an Msp porin whose diameter generally decreases from one end to the other along a central axis, where the narrowest portion of the vestibule is connected to the constriction zone. A vestibule may also be referred to as a "goblet." See FIG. 1 of WO 2010/034018 for an example of the vestibule of a wild-type MspA porin. The vestibule and the constriction zone together define the tunnel of an Msp porin.

When referring to a diameter of the vestibule of an Msp porin, it is understood that because the vestibule is cone-like in shape, the diameter changes along the path of a central axis, where the diameter is larger at one end than the opposite end. The diameter may range from about 2 nm to about 6 nm. Optionally, the diameter is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. The length of the central axis may range from about 2 nm to about 6 nm. Optionally, the length is about, at least about, or at most about 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 nm, or any range derivable therein. When referring to "diameter" herein, one may determine a diameter by measuring center-to-center distances or atomic surface-to-surface distances.

A "constriction zone" refers to the narrowest portion of the tunnel of an Msp porin, in terms of diameter, that is connected to the vestibule. The constriction zone of a wild-type MspA porin is shown in FIG. 1 of WO 2010/034018 (labeled "inner constriction"). The length of the constriction zone may range from about 0.3 nm to about 2 nm. Optionally, the length is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein. The diameter of the constriction zone may range from about 0.3 nm to about 2 nm. Optionally, the diameter is about, at most about, or at least about 0.3, 0.4, 0.5, 0.6, 0.7, 0.8, 0.9, 1.0, 1.1, 1.2, 1.3, 1.4, 1.5, 1.6, 1.7, 1.8, 1.9, 2, or 3 nm, or any range derivable therein.

A "neutral constriction zone" refers to a constriction zone comprising amino acid side chains that cumulatively exhibit no net electrical charge when immersed in an aqueous solution. The pH of the liquid medium (e.g., a buffered aqueous solution) in contact with the constriction zone may affect whether the constriction zone is characterized as neutral or not.

A "tunnel" refers to the central, empty portion of an Msp porin that is defined by the vestibule and the constriction zone, through which a gas, liquid, ion, or analyte may pass. A tunnel is an example of an opening of a nanopore.

A "mutant MspA porin" is a multimer complex that has at least or at most 70, 75, 80, 85, 90, 95, 98, or 99 percent or more identity, or any range derivable therein, but less than 100%, to its corresponding wild-type MspA porin and retains tunnel-forming capability. A mutant MspA porin may be recombinant protein. Optionally, a mutant MspA porin is one having a mutation in the constriction zone or the vestibule of a wild-type MspA porin. Optionally, a mutation may occur in the rim or the outside of the periplasmic loops of a wild-type MspA porin. A mutant MspA porin may be employed in any embodiment described herein.

Regarding the MspA porin in particular, optionally, the MspA porin is an octamer that consists of eight 184-amino acid MspA monomers. One or more mutations may take place in one or more of the amino acid MspA monomers of a wild-type MspA porin to yield a mutant MspA porin. In addition, an MspA porin may have fewer or more than eight monomers, any one or more of which may comprise a mutation.

Wild-type MspA porin comprises a periplasmic loop that consists of thirteen amino acids and is directly adjacent to the constriction zone. See J Biol Chem 284:10223 (2009). Wild-type MspB, C, and D porins also contain a periplasmic loop. One or more mutations may occur in the periplasmic loop of a wild-type Msp porin to generate a mutant Msp porin. For example, deletions of up to all thirteen amino acids may occur in the periplasmic loop of wild-type MspA porin. Typically, deletions in the periplasmic loop do not affect the tunnel-forming ability of an Msp porin.

An Msp porin or Msp monomer may also be chemically or biologically modified. For example, one may modify an Msp porin or Msp monomer with chemicals to produce disulfide bridges, as is known by those of skill in the art.

An Msp porin may comprise a nucleotide binding site. As used herein, a "nucleotide binding site" refers to a site in an Msp porin where a nucleotide stays in contact with, or resides at, an amino acid for a period of time that is longer than attributable to diffusion movement, such as greater than one picosecond or one nanosecond. Molecular dynamics calculations may be employed to assess these temporary resting times.

One or more mutations in an Msp porin may occur in the vestibule or the constriction zone of the protein. Optionally, a mutant Msp porin has at least one difference in its periplasmic loop, vestibule, or constriction zone amino acid sequence (e.g., deletion, substitution, addition) compared with the wild-type Msp porin. Other optional mutations are described herein.

The Msp porin of any embodiment herein may be any Msp porin described herein, such as a wild-type MspA porin, a mutant MspA porin, a wild-type MspA paralog or homolog porin, or a mutant MspA paralog or homolog porin. The Msp porin may be encoded by a nucleic acid sequence encoding a single-chain Msp porin. Any Msp porin here may comprise any Msp monomer described herein, such as a mutant Msp monomer.

Nutrients pass through wild-type porins in *mycobacteria*. Wild-type MspA porins, wild-type MspB porins, wild-type MspC porins, and wild-type MspD porins are examples of wild-type tunnel-forming porins. An Msp porin may be further defined as any Msp porin described herein, including paralogs, homologs, mutants and single-chain porins.

Exemplary wild-type MspA paralogs and homologs are provided in Table 2. Provided are wild-type MspA paralogs, which include wild-type MspB, wild-type MspC, and wild-type MspD. A "paralog," as defined herein, is a gene from the same bacterial species that has similar structure and function. A "homolog," as defined herein, is a gene from another bacterial species that has a similar structure and evolutionary origin. By way of an example, provided are wild-type MspA homologs, which include MppA, PorM1, PorM2, PorM1, and Mmcs4296.

TABLE 2

Exemplary wild-type MspA and wild-type MspA paralogs and homolog monomers

| Protein# | Organism | Identity/Similarity to MspA (%) | Length (aa) | Reference |
|---|---|---|---|---|
| MspA/Msmeg0965 | M. smegmatis | 100/100 | 211 | gb\|ABK74363.1\|, (Stahl et al., 2001)* |
| MspB/Msmeg0520 | M. smegmatis | 94/95 | 215 | gb\|ABK73437.1\|, (Stahl et al., 2001)* |
| MspC/Msmeg5483 | M. smegmatis | 93/95 | 215 | gb\|ABK74976.1\|, (Stahl et al., 2001)* |
| MspD/Msmeg6057 | M. smegmatis | 82/89 | 207 | gb\|ABK72453.1\|, (Stahl et al., 2001)* |
| MppA | M. phlei | 100/100 | 211 | AJ812030, (Dorner et al., 2004)** |
| PorM1 | M. fortuitum | 95/96 | 211 | emb\|CAI54228.1\| |
| PorM2 | M. fortuitum | 91/93 | 215 | emb\|CAL29811.1\| |
| PorM1 | M. peregrinum | 94/96 | 211 | emb\|CAI54230.1\| |
| Mmcs4296 | Mycobacterium sp. MCS | 85/91 | 216 | gb\|ABG10401.1\| |
| Mmcs4297 | Mycobacterium sp. MCS | 85/91 | 216 | gb\|ABG10402.1\| |
| Mmcs3857 | Mycobacterium sp. MCS | 30/44 | 235 | gb\|ABG09962.1\| |
| Mmcs4382 | Mycobacterium sp. MCS | 85/91 | 216 | gb\|ABL93573.1\| |
| Mmcs4383 | Mycobacterium sp. MCS | 85/91 | 216 | gb\|ABL93574.1\| |
| Mjls3843 | Mycobacterium sp. JLS | 26/40 | 235 | gb\|ABN99619.1\| |
| Mjls3857 | Mycobacterium sp. JLS | 26/40 | 235 | gb\|ABG09962.1\| |
| Mjls3931 | Mycobacterium sp. JLS | 26/40 | 235 | gb\|ABL93123.1\| |
| Mjls4674 | Mycobacterium sp. JLS | 85/89 | 216 | gb\|ABO00440.1\| |
| Mjls4675 | Mycobacterium sp. JLS | 83/89 | 216 | gb\|ABO00441.1\| |
| Mjls4677 | Mycobacterium sp. JLS | 84/89 | 216 | gb\|ABO00443.1\| |
| Map3123c | M. avium paratuberculosis | 24/39 | 220 | gb\|AAS05671.1\| |
| Mav3943 | M. avium | 24/39 | 227 | gb\|ABK66660.1\| |
| Mvan1836 | M. vanbaalenii PYR-1 | 82/88 | 209 | gb\|ABM12657.1\| |
| Mvan4117 | M. vanbaalenii PYR-1 | 32/43 | 239 | gb\|ABM14894.1\| |
| Mvan4839 | M. vanbaalenii PYR-1 | 83/88 | 209 | gb\|ABM15612.1\| |
| Mvan4840 | M. vanbaalenii PYR-1 | 83/89 | 209 | gb\|ABM15613.1\| |
| Mvan5016 | M. vanbaalenii PYR-1 | 30/41 | 238 | gb\|ABM15788.1\| |
| Mvan5017 | M. vanbaalenii PYR-1 | 25/35 | 227 | gb\|ABM15789.1\| |
| Mvan5768 | M. vanbaalenii PYR-1 | 21/32 | 216 | gb\|ABM16533.1\| |
| MUL_2391 | M. ulcerans Agy99 | 21/34 | 233 | gb\|ABL04749.1\| |
| Mflv1734 | M. gilvum PYR-GCK | 21/32 | 225 | gb\|ABP44214.1\| |
| Mflv1735 | M. gilvum PYR-GCK | 32/41 | 226 | gb\|ABP44215.1\| |
| Mflv2295 | M. gilvum PYR-GCK | 25/40 | 250 | gb\|ABP44773.1\| |
| Mflv1891 | M. gilvum PYR-GCK | 84/90 | 217 | gb\|ABP44371.1\| |
| MCH4691c | M. chelonae | 70/80 | 223 | gb\|ACV04474.1\| |
| MCH4689c | M. chelonae | 66/78 | 223 | gb\|ACV04472.1\| |
| MCH4690c | M. chelonae | 72/81 | 217 | gb\|ACV04473.1\| |
| MAB1080 | M. abscessus | 69/79 | 223 | emb\|CAM61170.1\| |
| MAB1081 | M. abscessus | 68/78 | 222 | emb\|CAM61171.1\| |
| MAB2800 | M. abscessus | 27/44 | 246 | emb\|CAM62879.1\| |
| RHA1 ro08561 | Rhodococcus jostii RHA1 | 34/51 | 233 | gb\|ABG99605.1\| |
| n.d. | Rhodococcus opacus B4 | 34/51 | 233 | gbj\|BAH52196.1\| |
| RHA1 ro04074 | Rhodococcus sp. RHA1 | 34/50 | 233 | gb\|ABG95871.1\| |
| RHA1 ro03127 | Rhodococcus sp. RHA1 | 34/50 | 233 | gb\|ABG94930.1\| |
| n.d. | Rhodococcus erythropolis PR4 | 35/50 | 229 | gbj\|BAH30938.1\| |

Only proteins with significant amino acid similarities over the full length of the protein were included. Data were obtained by PSI-Blast algorithm (BLOSUM62 matrix) using the NIH GenBank database on the world wide web at ncbi.nlm.nih.gov/blast/Blast.cgi.
n.d.: "not determined"
*Mol Microbiol 40: 451 (2001)
**Biochim Biophys Acta 1667: 47-55 (2004)

A "mutant MspA paralog or homolog porin" is a multimer complex that has at least or at most 70, 75, 80, 85, 90, 95, 98, or 99 percent or more identity, or any range derivable therein, but less than 100%, to its corresponding wild-type MspA paralog or homolog porin and retains tunnel-forming capability. A mutant MspA paralog or homolog porin may be recombinant protein. Optionally, a mutant MspA paralog or homolog porin is one having a mutation in the constriction zone or the vestibule of the wild-type MspA paralog or homolog porin. Optionally, a mutation may occur in the rim or the outside of the periplasmic loops of a wild-type MspA paralog or homolog porin. Any mutant MspA paralog or homolog porin may be employed in any embodiment described herein, and may comprise any mutation described herein.

An Msp porin may comprise two or more Msp monomers. An "Msp monomer" is a protein monomer that is either a wild-type MspA monomer, a mutant MspA monomer, a wild-type MspA paralog or homolog monomer, or a mutant MspA paralog or homolog monomer, and retains tunnel-forming capability when associated with one or more other Msp monomers. Any Msp porin described herein may comprise one or more of any Msp monomer as described herein. Any Msp porin may comprise, for example, 2-15 Msp monomers, wherein each monomer may be the same or different.

A "mutant MspA monomer" refers to an Msp monomer that has at least or at most 70, 75, 80, 85, 90, 95, 98, or 99 percent or more identity, or any range derivable therein, but less than 100%, to a wild-type MspA monomer, and retains tunnel-forming capability when associated with one or more other Msp monomers. Optionally, a mutant MspA monomer is further defined as comprising a mutation in that portion of the sequence that contributes to the formation of the vestibule or the constriction zone of a fully-formed, tunnel-forming porin. The mutant Msp monomer may be a recombinant protein, for example. A mutant MspA monomer may comprise any mutation described herein.

In any embodiment herein, an Msp monomer may be a wild-type MspA paralog or homolog, such as MspA/Msmeg0965, MspB/Msmeg0520, MspC/Msmeg5483, MspD/Msmeg6057, MppA, PorM1, PorM2, PorM1, Mmcs4296, Mmcs4297, Mmcs3857, Mmcs4382, Mmcs4383, Mjls3843, Mjls3857, Mjls3931 Mjls4674, Mjls4675, Mjls4677, Map3123c, May 3943, Mvan1836, Mvan4117, Mvan4839, Mvan4840, Mvan5016, Mvan5017, Mvan5768, MUL_2391, Mflv1734, Mflv1735, Mflv2295, Mflv1891, MCH4691c, MCH4689c, MCH4690c, MAB1080, MAB1081, MAB2800, RHA1 ro08561, RHA1 ro04074, and RHA1 ro03127.

A "mutant MspA paralog or homolog monomer" refers to an MspA paralog or homolog monomer that has at least or at most 70, 75, 80, 85, 90, 95, 98, or 99 percent or more identity, or any range derivable therein, but less than 100%, to a wild-type MspA paralog or homolog monomer, and retains tunnel-forming capability. Optionally, a mutant MspA paralog or homolog monomer is further defined as comprising a mutation in that portion of the sequence that contributes to the formation of the vestibule and/or the constriction zone of a fully-formed, tunnel-forming porin. The mutant MspA paralog or homolog monomer may be a recombinant protein, for example. Any mutant MspA paralog or homolog monomer may be optionally employed in any embodiment herein.

An Msp porin may be expressed as a combination of two or more wild-type MspA monomers, mutant MspA monomers, wild-type MspA paralog or homolog monomers, or mutant MspA paralog or homolog monomers. As such, an Msp porin may be or comprise a dimer, a trimer, a tetramer, a pentamer, a hexamer, a septamer, an octamer, a nonamer, etc. For example, an Msp porin may comprise a combination of wild-type MspA monomers and wild-type MspB monomers. An Msp porin may comprise 1-15 monomers, where each monomer is the same or different. Indeed, any Msp porin described herein may comprise at least or at most 1, 2, 3, 4, 5, 6, 7, 8, 9, 10, 11, 12, 13, 14, or 15 monomers, or any range derivable therein, where each monomer is the same or different. For example, an Msp porin may comprise one or more mutant MspA monomers that are the same or different. As another example, an Msp porin may comprise at least one mutant MspA monomer and at least one MspA paralog or homolog monomer.

As defined above, a single-chain Msp porin comprises two or more Msp monomers connected by one or more amino acid linker peptides. A single-chain Msp porin that comprises two Msp monomers, wherein the Msp monomers are linked by an amino acid linker sequence, may be referred to as a single-chain Msp porin dimer. A single-chain Msp porin that comprises eight Msp monomers, wherein the Msp monomers are linked by an amino acid linker sequence, may be referred to as a single-chain Msp porin octamer. A single-chain Msp porin may comprise 2, 3, 4, 5, 6, 7, 8, 9, 10, 11, 12, 13, 14, 15, or more Msp monomers, or any range derivable therein, linked by amino acid linker sequences. Optionally, a single-chain Msp porin can, for example, comprise two or more single-chain Msp porin dimers, two or more single-chain Msp porin trimers, two or more single-chain Msp porin quadrimers, two or more single-chain Msp porin pentimers, one or more single-chain Msp porin heximers, one or more single-chain Msp porin septimers, one or more single-chain Msp porin octamers, or combinations thereof. For example, a single-chain Msp porin can comprise a single-chain Msp porin dimer and two single-chain Msp porin trimers. By way of another example, a single-chain Msp porin can comprise a single-chain Msp porin quadrimer and two single-chain Msp porin dimers.

A wild-type single-chain Msp porin is comprised of wild-type Msp monomers. Optionally, one or more mutations in a single-chain Msp porin is present in the vestibule or the constriction zone of the single-chain Msp porin. The mutant single-chain Msp porin, for example, has at least one mutation in the amino acid sequence for the periplasmic loop, vestibule, or constriction zone (e.g., deletion, substitution, or addition) compared with a wild-type single-chain Msp. A multimer of single chains can also form a porin, wherein each single chain includes two, three, four, five, six, seven, or more Msp monomers.

Non-limiting examples of mutant MspA sequences are provided in Table 3. Optionally, the mutant MspA comprises an A to P substitution at amino acid 138, an E to A substitution at amino acid 139, or a combination thereof. Optionally, the mutant MspA comprises a D to K or R substitution at amino acid 90, a D to N substitution at amino acid 91, a D to N substitution at amino acid 93, or any combination thereof. Optionally, the mutant MspA comprises a D to Q substitution at amino acid 90, a D to Q substitution at amino acid 91, a D to N substitution at amino acid 93, or any combination thereof. Optionally, the mutant MspA comprises a L to W substitution at amino acid 88, an I to W substitution at amino acid 105, a D to Q substitution at amino acid 91, a D to N substitution at amino acid 93, or any combination thereof. Optionally, the mutant MspA comprises an I to W substitution at amino acid 105, a N to W substitution at amino acid 108, or a combination thereof. Optionally, the mutant MspA comprises a D to R substitution at amino acid 118, an E to K substitution at amino acid 139, a D to R substitution at amino acid 134, or any combination thereof. For the mutant MspB monomer sequences listed below, the reference MspB sequence is the mature wild-type MspB monomer sequence, which is known in the art. Optionally, the mutant MspB comprises a D to K or R substitution at amino acid 90, a D to N substitution at amino acid 91, a D to N substitution at amino acid 93, or any combination thereof.

TABLE 3

| MspA mutants | |
| --- | --- |
| Row 1 | Row 2 |
| MspA D90A | MspA T84C |
| MspA D91A | MspA I87C |
| MspA D90A/D91A | MspA D91C |

TABLE 3-continued

MspA mutants

| Row 1 | Row 2 |
|---|---|
| MspA D90E | MspA D93C |
| MspA D91E | MspA A96C |
| MspA D90E/D91E | MspA P97C |
| MspA D90F | MspA G100C |
| MspA D91F | MspA N102C |
| MspA D90F/D91F | MspA P107C |
| MspA D90G | MspA G112C |
| MspA D91G | MspA V113C |
| MspA D90G/D91G | MspA S114C |
| MspA D90H | MspA D118C |
| MspA D91H | MspA N121C |
| MspA D90H/D91H | MspA E127C |
| MspA D90K | MspA F131C |
| MspA D91K | MspA D134C |
| MspA D90K/D91K | MspA S136C |
| MspA D90L | MspA A138C |
| MspA D91L | MspA E139C |
| MspA D90L/D91L | MspA G141C |
| MspA D90R | MspA V144C |
| MspA D91R | MspA H148C |
| MspA D90R/D91R | MspA T150C |
| MspA D90S | MspA A155C |
| MspA D91S | MspA R161C |
| MspA D90S/D91S | MspA R165C |
| MspA D90W | MspA S173C |
| MspA D91W | MspA T175C |
| MspA D90W/D91W | MspA E179C |
| MspA D90Y | MspA V184C |
| MspA D91Y | MspA N79C/D90K/D91N/P97C |
| MspA D90Y/D91Y | MspA K47S/D90K/D91N/P97C/D134C |
| MspA Q126C | MspA ΔA96-P98 |
| MspA D90N | MspA ΔT95-F99 |
| MspA D91N | MspA ΔI94-G100 |
| MspA D93N | MspA ΔD93-L101 |
| MspA D90N/D91N | MspA ΔG92-N102 |
| MspA D90N/D91N/D93N | MspA N79R/D90N/D91N/D93N |
| MspA D90Q/D91N/D93N | MspA N79W/D90N/D91N/D93N |
| MspA D90Q/D91Q/D93N | MspA D90N/D91N/D93N/Q126R |
| MspA D90T/D91N/D93N | MspA D90N/D91N/D93N/T130R |
| MspA D90T/D91T/D93N | MspA D90N/D91N/D93N/D134R |
| MspA D91E | MspA D90N/D91N/D93N/Q126W |
| MspA D90E | MspA D90N/D91N/D93N/T130W |
| MspA D90E/D91E | MspA D90N/D91N/D93N/D134W |
| MspA D90N/D91N/D93Q | MspA D90N/D91N/D93N/D118W/D134R/E139K |
| MspA D90N/D91N/G92Q/D93N | MspA D90N/D91N/D93N/D118F/D134R/E139K |
| MspA G1C | MspA D90N/D91N/D93N/D118H/D134R/E139K |
| MspA D3C | MspA D90N/D91N/D93N/D118Y/D134R/E139K |
| MspA E5C | MspA N79W/D90N/D91N/D93N/D118R/E139K |
| MspA D10C | MspA N79F/D90N/D91N/D93N/D118R/E139K |
| MspA D13C | MspA N79H/D90N/D91N/D93N/D118R/E139K |
| MspA R14C | MspA N79Y/D90N/D91N/D93N/D118R/E139K |
| MspA T17C | MspA D90N/D91K/D93N |
| MspA W21C | MspA D90N/D91R/D93N |
| MspA D22C | MspA D90N/D91W/D93N |
| MspA G27C | MspA D90N/D91W/D93N |
| MspA R33C | MspA D90N/D91T/D93N |
| MspA R38C | MspA D90N/D91L/D93N |
| MspA G44C | MspA D90N/D91H/D93N |
| MspA K47C | MspA D90N/D91S/D93N |
| MspA I49C | MspA D90N/D91N/D93N/D118R |
| MspA E57C | MspA D90N/D91N/D93N/D118R/E139R |
| MspA G60C | MspA D90N/D91N/D93N/D118R/E139K |
| MspA E63C | MspA D90N/D91N/D93N/D118R/D134R/E139K |
| MspA G69C | MspA D90Q/D91N/D93N/D118R/D134R/E139K |
| MspA S73C | MspA D90Q/D91Q/D93N/D118R/D134R/E139K |
| MspA L74C | MspA D90T/D91N/D93N/D118R/D134R/E139K |
| MspA V76C | MspA D90T/D91T/D93N/D118R/D134R/E139K |

An MspA monomer may comprise one or more mutations at any of the following amino acid positions: 88, 105, 108, 118, 134, or 139. An MspA monomer may comprise one or more of the following mutations: L88W, D90K/N/Q/R, D91N/Q, D93N, I105W, N108W, D118R, D134R, or E139K. An MspA monomer may comprise the following mutations: D90N/D91N/D93N. An MspA monomer may comprise the following mutations: D90N/D91N/D93N/D118R/D134R/E139K. An MspA monomer may comprise the following mutations: D90Q/D91Q/D93N. An MspA monomer may comprise the following mutations: D90Q/D91Q/D93N/D118R/D134R/E139K. An MspA monomer may comprise the following mutations: D90(K,R)/D91N/D93N. An MspA monomer may comprise the following mutations: (L88,I105) W/D91Q/D93N. An MspA monomer may comprise the following mutations: I105W/N108W. Moreover, an MspA monomer may comprise any other mutation described herein.

In any embodiment herein, a mutant Msp porin, such as a mutant MspA porin or a mutant MspA paralog or homolog, may comprise at least one additional positively charged amino acid compared to the vestibule or the constriction zone of a wild-type Msp porin, respectively; at least one additional negatively charged amino acid compared to the vestibule or the constriction zone of a wild-type MspA porin, respectively; at least one less positively charged amino acid compared to the vestibule or the constriction zone of a wild-type MspA porin, respectively; or at least one less negatively charged amino acid compared to the vestibule or the constriction zone of a wild-type MspA porin, respectively.

Optionally, each positively charged amino acid in the vestibule and the constriction zone of a wild-type Msp porin is replaced with a negatively charged amino acid, and each negatively charged amino acid is the same or different; or each negatively charged amino acid in the vestibule and the constriction zone of a wild-type Msp porin is replaced with a positively charged amino acid, and each positively charged amino acid is the same or different.

Optionally, the vestibule or the constriction zone of a mutant Msp porin comprises a greater number of positively charged residues than that of the vestibule or the constriction zone of a wild-type Msp porin, respectively; or the vestibule or the constriction zone comprises a greater number of negatively charged residues than that of the vestibule or the constriction zone of a wild-type Msp porin, respectively; or at least one positively charged amino acid in the vestibule or the constriction zone of a wild-type Msp porin, such as wild-type MspA porin or a wild-type MspA paralog or homolog porin, is either deleted or replaced by a negatively charged amino acid; or at least one negatively charged amino acid in the vestibule or the constriction zone of a wild-type Msp porin is either deleted or replaced by a positively charged amino acid.

At least one amino acid in the vestibule or the constriction zone of a wild-type Msp porin, such as a wild-type MspA porin or a wild-type MspA paralog or homolog porin, may be substituted by an amino acid having a sterically larger side chain; an amino acid having a sterically smaller side chain; an amino acid having a more polar side chain; an amino acid having a less polar side chain; or an amino acid having a more hydrophobic side chain; an amino acid having a less hydrophobic side chain.

In any embodiment herein, at least one amino acid in the vestibule or the constriction zone of a mutant Msp porin may comprise an unnatural amino acid or a chemically modified amino acid.

A mutant Msp porin, such as a mutant MspA porin or a mutant MspA paralog or homolog porin, may comprise a neutral constriction zone. A mutant Msp porin, such as a mutant MspA porin or a mutant MspA paralog or homolog porin, may comprise a conductance through the tunnel that is higher, such as two-fold higher, than the conductance through the tunnel of its corresponding wild-type Msp porin. A mutant Msp porin, such as a mutant MspA porin or a mutant MspA paralog or homolog porin, may comprise a conductance through the tunnel that is lower than the conductance through the tunnel of its corresponding wild-type Msp porin.

Any Msp porin discussed herein may comprise a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel. Also provided herein is a mutant MspA porin comprising a vestibule having a length from about 2 to about 6 nm and a diameter from about 2 to about 6 nm, and a constriction zone having a length from about 0.3 to about 3 nm and a diameter from about 0.3 to about 3 nm, wherein the vestibule and constriction zone together define a tunnel, and further comprising at least a first mutant MspA paralog or homolog monomer.

The diameter of the constriction zone of a mutant Msp porin, such as a mutant MspA porin or mutant MspA paralog or homolog, may be less than the diameter of the constriction zone of its corresponding wild-type Msp porin, such as a wild-type MspA porin or wild-type MspA paralog or homolog. A mutant Msp porin, such as a mutant MspA porin or mutant MspA paralog or homolog, may comprise a mutation in the vestibule or the constriction zone that permits an analyte to have a velocity or an average velocity as it interacts with the tunnel that is less than the velocity or average velocity at which the analyte interacts with the tunnel of its corresponding wild-type Msp porin, (e.g., wild-type MspA porin, wild-type MspA paralog or homolog).

Sequences of wild-type Msp monomers discussed herein are disclosed in GenBank, located on the world wide web at pubmed.gov, and these sequences and others are herein incorporated by reference in their entireties as are individual subsequences or fragments contained therein. For example, the nucleotide and amino acid sequences of a wild-type MspA monomer can be found at GenBank Accession Nos. AJ001442 and CAB56052, respectively. The nucleotide and amino acid sequences of a wild-type MspB monomer can be found, for example, at GenBank Accession Nos. NC_008596.1 (from nucleotide 600086 to 600730) and YP_884932.1, respectively. The nucleotide and amino acid sequences of a wild-type MspC monomer can be found, for example, at GenBank Accession Nos. AJ299735 and CAC82509, respectively. The nucleotide and amino acid sequences of a wild-type MspD monomer can be found, for example, at GenBank Accession Nos. AJ300774 and CAC83628, respectively. Thus provided are the nucleotide sequences of MspA, MspB, MspC, and MspD monomers comprising a nucleotide sequence at least about 70, 75, 80, 85, 90, 95, 98, 99 percent or more, or any range derivable therein, identical to the nucleotide sequence of the aforementioned nucleotide GenBank Accession Numbers. Amino acid sequences of MspA, MspB, MspC, and MspD monomers may be found in FIG. 18 of WO 2010/034018 comprising an amino acid sequence at least about 70, 75, 80, 85, 90, 95, 98, 99 percent or more, or any range derivable therein, identical to the sequences of the aforementioned amino acid GenBank Accession Numbers.

Also provided are amino acid sequences of MspA paralogs and homolog monomers comprising an amino acid sequence at least about 70, 75, 80, 85, 90, 95, 98, 99 percent or more, or any range derivable therein to a wild-type MspA paralog or homolog monomer. Wild-type MspA paralog and homolog monomers are well-known in the art. See Table 2.

The α-hemolysin pore is formed of seven identical subunits (heptameric). The polynucleotide sequence that encodes one subunit of α-hemolysin is shown in SEQ ID NO: 1 of U.S. Publ. Appl. Serial No. 2010/0196203, incorporated herein by reference in its entirety. The full-length amino acid sequence of one subunit of α-hemolysin is shown in SEQ ID NO: 2 of U.S. Publ. Appl. Serial No. 2010/0196203. The first 26 amino acids of SEQ ID NO: 2 correspond to the signal peptide. The amino acid sequence of one mature subunit of α-hemolysin without the signal peptide is shown in SEQ ID NO: 3 of U.S. Publ. Appl. Serial No. 2010/0196203. SEQ ID NO: 3 has a methionine residue at position 1 instead of the 26 amino acid signal peptide that is present in SEQ ID NO: 2.

A variant is a heptameric pore in which one or more of the seven subunits has an amino acid sequence which varies from that of SEQ ID NO: 2 or 3 and which retains pore activity. 1, 2, 3, 4, 5, 6 or 7 of the subunits in a mutant α-hemolysin may have an amino acid sequence that varies from that of SEQ ID NO: 2 or 3. The seven subunits within a mutant pore are typically identical but may be different.

The mutant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2 or 3, a variant may be at least 50% homologous to that sequence based on amino acid identity. The subunit polypeptide may be at least 80%, at least 90%, at least 95%, at least 98%, at least 99% homologous based on amino acid identity to the amino acid sequence of SEQ ID NO: 2 or 3 over the entire sequence.

Amino acid substitutions may be made to the amino acid sequence of SEQ ID NO: 2 or 3, for example a single amino acid substitution may be made or two or more substitutions may be made. In some embodiments, replacement of the lysine at position 34 in SEQ ID NO: 2 and position 9 in SEQ ID NO: 3 with cysteine (i.e. K34C or K9C). Another example of a non-conservative substitution that may be made is the replacement of the asparagine residue at position 43 of SEQ ID NO: 2 or position 18 of SEQ ID NO: 3 with cysteine (i.e. N43C or N17C). The inclusion of these cysteine residues in SEQ ID NO: 2 or 3 provides thiol attachment points at the relevant positions. Similar changes could be made at all other positions, and at multiple positions on the same subunit.

In some embodiments, one or more amino acid residues of the amino acid sequence of SEQ ID NO: 2 or 3 may alternatively or additionally be deleted. Up to 50% of the residues may be deleted, either as a contiguous region or multiple smaller regions distributed throughout the length of the amino acid chain.

Variants can include subunits made of fragments of SEQ ID NO: 2 or 3. Such fragments retain their ability to insert into a bilayer. Fragments can be at least 100, such as 150, 200 or 250, amino acids in length. Such fragments may be used to produce chimeric pores. A fragment may comprise the β-barrel domain of SEQ ID NO: 2 or 3.

Variants include chimeric proteins comprising fragments or portions of SEQ ID NO: 2 or 3. Chimeric proteins are formed from subunits each comprising fragments or portions of SEQ ID NO: 2 or 3. The β-barrel part of chimeric proteins are typically formed by the fragments or portions of SEQ ID NO: 2 or 3.

One or more amino acid residues may alternatively or additionally be inserted into, or at one or other or both ends of, the amino acid sequence SEQ ID NO: 2 or 3. Insertion of one, two or more additional amino acids to the C terminal end of the peptide sequence is less likely to perturb the structure and/or function of the protein, and these additions could be substantial, but peptide sequences of up to 10, 20, 50, 100 or 500 amino acids or more can be used. Additions at the N terminal end of the monomer could also be substantial, with one, two or more additional residues added, but also 10, 20, 50, 500 or more residues being added. Additional sequences can also be added to the protein in the trans-membrane region, between amino acid residues 119 and 139 of SEQ ID NO: 3. More precisely, additional sequences can be added between residues 127 and 130 of SEQ ID NO: 3, following removal of residues 128 and 129. Additions can be made at the equivalent positions in SEQ ID NO: 2. A carrier protein may be fused to an amino acid sequence according to the invention.

Other optional mutations are described herein.

OmpATb is an outer membrane protein present in e.g., *M. tuberculosis* and *M. bovis*|$_{[isc1]}$. OmpATb's pore-forming activity is pH-dependent, enabling *mycobacteria* to survive in acidic environmental conditions. The sequences of OmpATb in both *M. tuberculosis* and *M. bovis* are identical. See FIG. 1 of U.S. Publ. Appl. No. 2010/0150966, incorporated herein by reference in its entirety.

The term "OmpATb" comprises the native form of the protein in *mycobacteria* as well as recombinant proteins produced in any type of expression vectors transforming any kind of host, or also chemically synthesized proteins or peptides. It also includes analog proteins, i.e. proteins with minor variations not affecting the antigenicity of OmpATb, e.g., proteins having at least 70% sequence identity to the sequence of OmpATb. Other optional mutations are described herein.

Descriptions of additional optional substitutions that may be made with respect to Msp porins, Msp monomers, α-hemolysin and variants thereof, and OmpATb and other proteins provided herein are described below.

Protein modifications described herein include amino acid sequence modifications. Modifications in amino acid sequence may arise naturally as allelic variations (e.g., due to genetic polymorphism), may arise due to environmental influence (e.g., due to exposure to ultraviolet radiation), or may be produced by human intervention (e.g., by mutagenesis of cloned DNA sequences), such as induced point, deletion, insertion, and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions may be made in adjacent pairs, i.e., a deletion of 2 residues or insertion of 2 residues. Substitutions, deletions, insertions or any combination thereof may be combined to arrive at a final construct. The mutations may or may not place the sequence out of reading frame and may or may not create complementary regions that could produce secondary mRNA structure. Substitutional modifications are those in which at least one residue has been removed and a different residues inserted in its place.

Modifications, including the specific amino acid substitutions, are made by known methods. By way of example, modifications are made by site specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example M13 primer mutagenesis and PCR mutagenesis.

The peptides, polypeptides, monomers, multimers, proteins, etc. described herein can be further modified and varied so long as the desired function is maintained or enhanced. It is understood that one way to define any known modifications and derivatives or those that might arise, of the disclosed genes and proteins herein is through defining the modifications and derivatives in terms of identity to specific known sequences. Specifically disclosed are polypeptides which have at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to a wild-type MspA and wild-type MspA paralogs or homologs (e.g., wild-type MspB, wild-type MspC, wild-type MspD, MppA, PorM1, Mmcs4296) and mutants provided herein as well as α-hemolysin and variants thereof and OmpATb.

Those of skill in the art readily understand how to determine the identity of two polypeptides. For example, the identity can be calculated after aligning the two sequences so that the identity is at its highest level. For example, to determine the "percent identity" of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., percent identity=number of identical positions/total number of positions (e.g., overlapping positions)×100). In one embodiment, the two sequences are the same length.

Several methods exist for determining percent identity. One may determine percent identity in the following manner. A target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from the U.S. government's National Center for Biotechnology Information web site (world wide web at ncbi.nlm.nih.gov). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options may be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; –o is set to any desired file name (e.g., C:\output.txt); -q is set to –1; -r is set to 2; and all other options are left at their default setting. The following command will generate an output file containing a comparison between two sequences: C:\Bl2seq -i c:\seq1.txt -j c:\seq2.txt -p blastn -o c:\output.txt -q –1 -r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length may be determined by counting the number of matched positions over that length and dividing that number by the length followed by multiplying the resulting value by 100. For example, if (1) a 50 nucleotide target sequence is compared to the sequence encoding wild-type MspA (2) the Bl2seq program presents 45 nucleotides from the target sequence aligned with a region of the sequence encoding wild-type MspA where the first and last nucleotides of that 45 nucleotide region are matches, and (3) the number of matches over those 45 aligned nucleotides is 40, then the 50 nucleotide target sequence contains a length of 45 and a percent identity over that length of 89 (i.e., 40/45×100=89).

Another way of calculating identity can be performed by published algorithms. Optimal alignment of sequences for comparison may be conducted by the local identity algorithm of Smith and Waterman, Adv Appl Math 2:482 (1981), by the identity alignment algorithm of Needleman and Wunsch, J Mol Biol 48:443 (1970), by the search for similarity method of Pearson and Lipman, Proc Natl Acad Sci USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Science 244:48-52 (1989); Proc Natl Acad Sci USA 86:7706-10 (1989); and Methods Enzymol 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity and to be disclosed herein.

Nucleic acids that encode protein sequences disclosed herein, as well as variants and fragments thereof, are also disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

Fragments and partial sequences of proteins may be useful in methods described herein. As with all peptides and proteins, including fragments thereof, it is understood that additional modifications in the amino acid sequences of the proteins disclosed herein can occur that do not alter the nature or function of the peptides and proteins. It will be appreciated that the only limitation on these is practical, they must comprise the necessary functional elements (e.g., tunnel-forming capability) for use in the relevant embodiment. Such modifications include conservative amino acids substitutions and are discussed in greater detail below.

The following table provides non-limiting examples of properties of amino acids that may assist a skilled artisan in determining how to select amino acids for modifications of proteins (e.g., protein pores) as described herein.

TABLE 4

Amino Acid Properties

| Amino Acid | Percent Buried Residues[a] (%) | Average Volume[b] (Å³) | van der Waals volume[c] (Å³) | Accessible surface area[d] (Å²) | Ranking of amino acid polarities[e] |
|---|---|---|---|---|---|
| alanine | 38 (12) | 92 | 67 | 67 | 9 (7) |
| arginine | 0 | 225 | 148 | 196 | 15 (19) |
| asparagine | 10 (2) | 135 | 96 | 113 | 16 (16) |
| aspartic acid | 14.5 (3) | 125 | 91 | 106 | 19 (18) |
| cysteine | 47 (3) | 106 | 86 | 104 | 7 (8) |
| glutamine | 6.3 (2.2) | 161 | 114 | 144 | 17 (14) |
| glutamic acid | 20 (2) | 155 | 109 | 138 | 18 (17) |
| glycine | 37 (10) | 66 | 48 | | 11 (9) |
| histidine | 19 (1.2) | 167 | 118 | 151 | 10 (13) |
| isoleucine | 65 (12) | 169 | 124 | 140 | 1 (2) |
| leucine | 41 (10) | 168 | 124 | 137 | 3 (1) |
| lysine | 4.2 (0.1) | 171 | 135 | 167 | 20 (15) |
| methionine | 50 (2) | 171 | 124 | 160 | 5 (5) |
| phenylalanine | 48 (5) | 203 | 135 | 175 | 2 (4) |
| proline | 24 (3) | 129 | 90 | 105 | 13 (—) |
| serine | 24 (8) | 99 | 73 | 80 | 14 (12) |
| threonine | 25 (5.5) | 122 | 93 | 102 | 12 (11) |
| tryptophan | 23 (1.5) | 240 | 163 | 217 | 6 (6) |
| tyrosine | 13 (2.2) | 203 | 141 | 187 | 8 (10) |
| valine | 56 (15) | 142 | 105 | 117 | 4 (3) |

[a]This column represents the tendency of an amino acid to be buried (defined as <5% of residue available to solvent) in the interior of a protein and is based on the structures of nine proteins (total of ~2000 individual residues studied, with 587 (29%) of these buried). Values indicate how often each amino acid was found buried, relative to the total number of residues of this amino acid found in the proteins. Values in parentheses indicate the number of buried residues of this amino acid found relative to all buried residues in the proteins. Data from BioTechnology 8: 308 (1990); for other calculation methods with similar results, see Nature 277: 491 (1979); and Science 229: 834 (1985).
[b]Average volume ($V_r$) of buried residues, calculated from the surface area of the side chain. Annu Rev Biophys Bioeng 6: 151 (1977); Protein Eng 2: 329 (1989).
[c]Data from Darby N. J. and Creighton T. E. Protein structure. In In focus (ed. D. Rickwood), p. 4. IRL Press, Oxford, United Kingdom (1993).
[d]Total accessible surface area (ASA) of amino acid side chain for residue X in a Gly-X-Gly tripeptide with the main chain in an extended conformation. J Mol Biol 196: 641 (1987).
[e]Values shown represent the mean ranking of amino acids according to the frequency of their occurrence at each sequence rank for 38 published hydrophobicity scales. Protein Eng 11: 153 (1998). Although the majority of these hydrophobicity scales are derived from experimental measurements of chemical behavior or physico-chemical properties (e.g., solubility in water, partition between water and organic solvent, chromatographic migration, or effects on surface tension) of isolated amino acids, several "operational" hydrophobicity scales based on the known environment characteristics of amino acids in proteins, such as their solvent accessibility or their inclination to occupy the core of proteins (based on the position of residues in the teritary structures as observed by x-ray crystallography or NMR) are included. The lower rankings represent the most hydrophobic amino acids, and higher values represent the most hydrophilic amino acids. For comparative purposes, the hydrophobicity scale of Radzicka and Wolfenden, Biochem 27: 1664 (1988) is shown in parentheses. That scale was derived from the measured hydration potential of amino acids that is based on their free energies of transfer from the vapor phase to cyclohexane, 1-octanol, and neutral aqueous solution.

Alternatively, one may consider the hydropathic index of amino acids. Each amino acid has been assigned a hydropathic index on the basis of their hydrophobicity and/or charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and/or arginine (−4.5). The importance of the hydropathic amino acid index in conferring interactive biological function on a protein is generally understood in the art. It is known that certain amino acids may be substituted for other amino acids having a similar hydropathic index and/or score and/or still retain a similar biological activity. In making changes based upon the hydropathic index, the substitution of amino acids whose hydropathic indices may be within ±2; within ±1, or within ±0.5.

It also is understood in the art that the substitution of like amino acids can be made effectively on the basis of hydrophilicity. As detailed in U.S. Pat. No. 4,554,101, incorporated herein by reference, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). In making changes based upon similar hydrophilicity values, it is contemplated that the substitution of amino acids whose hydrophilicity values may be within ±2, within ±1, or those within ±0.5.

Any mutant protein may comprise a conservative amino acid substitution as compared to a wild-type Msp porin or monomer. Any substitution mutation is conservative in that it minimally disrupts the biochemical properties of the protein. Non-limiting examples of mutations that are introduced to substitute conservative amino acid residues include: positively-charged residues (e.g., H, K, and R) substituted with positively-charged residues; negatively-charged residues (e.g., D and E) substituted with negatively-charged residues; neutral polar residues (e.g., C, G, N, Q, S, T, and Y) substituted with neutral polar residues; and neutral non-polar residues (e.g., A, F, I, L, M, P, V, and W) substituted with neutral non-polar residues. Conservative substitutions may made in accordance with the following Table 5. Nonconservative substitutions can be made as well (e.g., proline for glycine).

TABLE 5

Exemplary Amino Acid Substitutions

| Amino Acid | Substitutions |
| --- | --- |
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |
| Tyr | Trp, Phe, His |
| Val | Ile, Leu, Met |

A nanopore will typically be able to be inserted in a lipid bilayer or other thin film, and these techniques are well-known in the art, as explained herein. In addition, U.S. Pat. No. 6,746,594, incorporated herein by reference, describes a variety of lipid bilayers and thin films, including inorganic materials, that may be employed with respect to the nanopores discussed herein. Methods, apparatuses, and techniques described in U.S. Pat. No. 6,267,872, incorporated herein by reference in its entirety, are also employable with respect to nanopores discussed herein.

In some embodiments, a plurality of nanopores are comprised in an artificial membrane comprising a mycolic acid. For example, 2, 3, 4, 5, 10, 20, 200, 2000, or more may be comprised in a membrane.

Optionally, 2, 3, 4, 5, 10, 20, 200, 2000, or more nanopores are comprised in a membrane, bilayer, or thin film. Indeed, anywhere from 2 to $10^{10}$ nanopores may be employed in embodiments described herein. Such a plurality of nanopores may be in the form of clusters of nanopores. Clusters may be randomly assembled or may adopt a pattern. As used herein, a "cluster" refers molecules that are grouped together and move as a unit, but are not covalently bound to one another.

As an alternative to or in addition to "comprising," any embodiment herein may recite "consisting of:" The transitional phrase "consisting of" excludes any element, step, or ingredient not specified in the claim.

Any embodiment herein may optionally exclude any other embodiment herein.

The use of the term "or" in the claims is used to mean "and/or" unless explicitly indicated to refer to alternatives only or the alternatives are mutually exclusive, although the disclosure supports a definition that refers to only alternatives and "and/or."

Throughout this application, the term "about" is used to indicate that a value includes the standard deviation of error for the device or method being employed to determine the value. In any embodiment discussed in the context of a numerical value used in conjunction with the term "about," it is specifically contemplated that the term about can be omitted.

Following long-standing patent law, the words "a" and "an," when used in conjunction with the word "comprising" in the claims or specification, denotes one or more, unless specifically noted.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed. It is therefore contemplated that any embodiment discussed in this specification can be implemented with respect to any method, system, or composition, etc., described herein, and vice versa. For example, any nanopore described herein can be employed in any method described herein.

EXAMPLES

Example 1

Materials and Methods Used in Examples 1-5

The experimental setup used in the following examples has been described previously (Biophys J 77, 3227 (1999) and Biophys J 90:190 (2006)). Briefly, a 20-90 μm Teflon® aperture is formed by melting Teflon® heat shrink tubing (Small Parts, Inc) around a finely sharpened needle or a wire. After removing the needle or wire, the tubing is cut to form an aperture of the desired width. The tubing is then bent to connect two ~200 μL wells in a Teflon® holder. Ag—AgCl electrodes are used to ground the resultant cis well and connect the trans well to either an Axopatch™ 200B, 1B or 1C patch clamp amplifier operated in voltage clamp mode. To find the membrane rupture voltage of the MA membranes, which exceeded the 1.2 V maximum output voltage of the patch clamp amplifiers, a variable power supply in series was used with a Keithley® 485 picoammeter. A 1.0 M KCl solution in DI water, buffered to pH 8.0+/−0.05 with 10 mM HEPES, electrically connects the two wells.

Ion channel currents are sampled at 250 kHz or 500 kHz and low-pass filtered with a 4-pole Bessel filter at ⅕ the sampling rate. Data acquisition was controlled by custom software written in LabWindows® and LabVIEW®. For lifetime measurements, data were sampled at 10 Hz.

Example 2

Artificial Mycolic Acid Membrane Formation

Mycolic acids were purchased (≥98%, Sigma-Aldrich, St. Louis, Mo.) that are extracted from *M. tuberculosis* and are dissolved in chloroform to 50 g/L and stored at −20° C. until use. The mycolic acid membranes are formed using the painting technique, widely used in similar experiments with dipalmitoylphosphatidylcholine (DPhPC) (Biophys J 77:3227 (1999)). The process began with two preparatory steps. In the first step the Teflon® aperture was pretreated with a coat of a lipid-hexane mixture. 1 µL of the MA/chloroform solution was air dried in a glass test tube, then resuspended in 0.01 g hexane. 1 µL of the resuspended MA pretreating solution was applied to the cis side of the Teflon® aperture and then gentle air pressure was applied with a syringe from the trans side to clear the aperture as the hexane evaporates. After clearing the solution from the aperture once, another 1 µL of pretreating solution was applied and cleared. After allowing the system to air dry for 15 minutes, an electrical connection between the two electrodes was established by putting the KCl buffer in the aperture, tube and the wells.

In the second preparatory step the lipid was painted on the aperture. 10 µL of the MA/chloroform solution was air dried on a chloroform-cleaned glass slide. Then, ~0.1 µL hexadecane was applied onto the MA and the solution was heated to 35° C. for approximately 5 min to promote incorporation of the hexadecane into the lipid. When the MA-hexadecane mixture reached a gel-like consistency, a ~1 mm diameter blob of the mixture was applied to a single bristle brush. While monitoring the ion current through the aperture, the lipid-solvent mixture was gently applied over the Teflon® aperture until the current fell to zero. Manually forcing buffer through the aperture from the trans side eliminated the physical blockage. For apertures greater than 40 µm in diameter, the lipid was applied to the outer edge of the aperture rather than over the top of the aperture.

The membranes was formed by placing a 3-6 µL air bubble over the prepared aperture using a micropipette and then the air bubble was gently retracted. Membrane formation was indicated by the current through the aperture sharply falling to zero. If nanopores can form within the lipid system the presence of a bilayer membrane is assumed, and not a multilamellar lipid structure or a physical lipid obstruction. Observation of these pores is described below.

Example 3

Determining Properties of the Artificial Mycolic Acid Membranes

Figure 2:
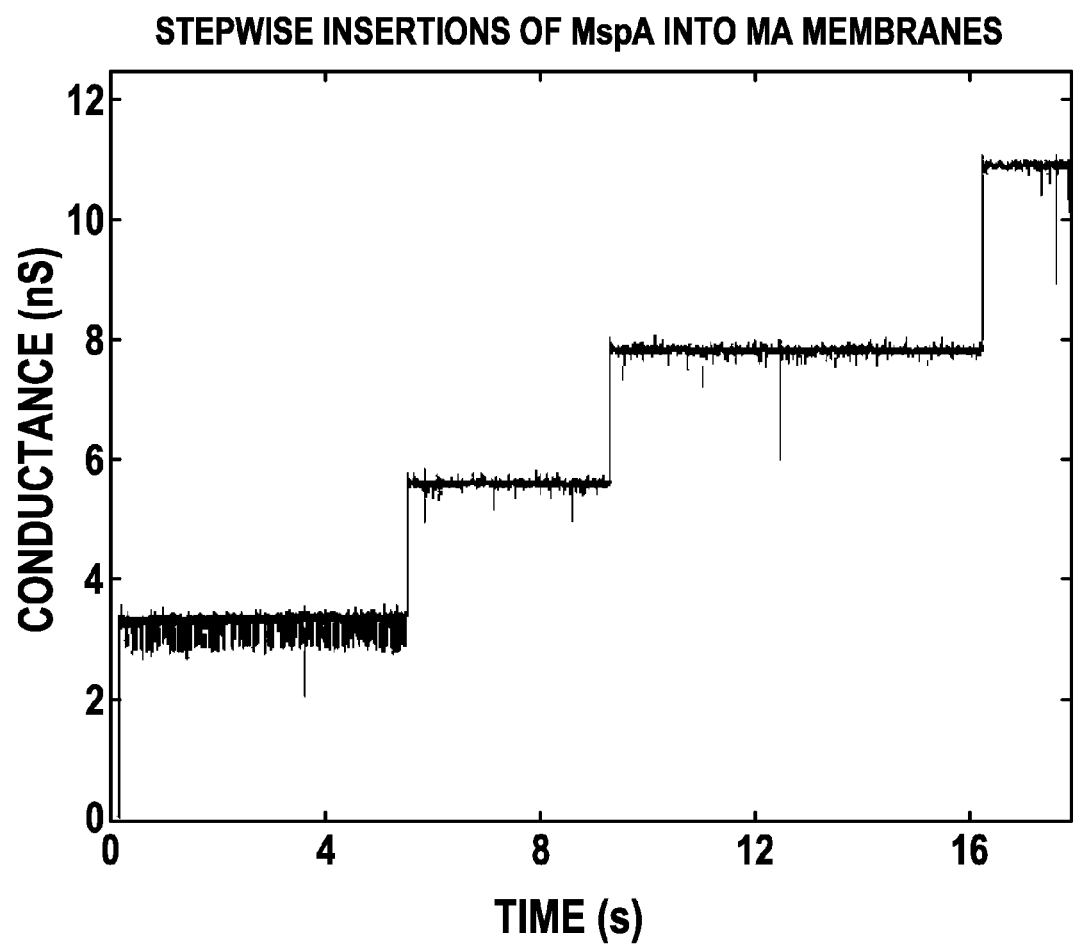
FIG. 2 shows change in conductivity across mycolic acid (MA) membranes with discrete current steps after the addition of MspA. The observed current steps are indistinguishable from current levels observed in DPhPC membranes.

Formation. The MA membranes were formed with similar reliability to DPhPC membranes. Also, MspA incorporated similarly into both MA (FIG. 2) and DPhPC membranes at ~0.2 pores/second with a concentration of ~10 nM MspA. The MspA pores in the MA membranes lasted for several hours before spontaneously leaving the membrane, similar to the behavior of MspA pores in DPhPC membranes.

MspA has a height of approximately 9 nm and a hydrophobic length of only ~5 nm that limit the hydrophobic barrier size that the nanopore can penetrate. In vivo, the outer membranes of *Mycobacteria* are ~8 nm. If the membrane consisted of two or more layers of MA (with an oil layer separating the two) MspA would be unable to span the membrane. Therefore the insertion of the transmembrane MspA pore within the MA system strongly suggests the formation of bilayer membranes instead of other lipid configurations.

Membrane resistance, rupture, capacitance and longevity. MA membranes were examined using the Axopatch® amplifier to determine a lower bound of their resistance. On the 20-40 µm apertures the measured ion current was <1 pA when ±1.2 V was applied across the membrane, corresponding to >1 TΩ resistance. DPhPC membranes formed on the same apertures also exhibited resistance values >1 TΩ.

Figure 3:
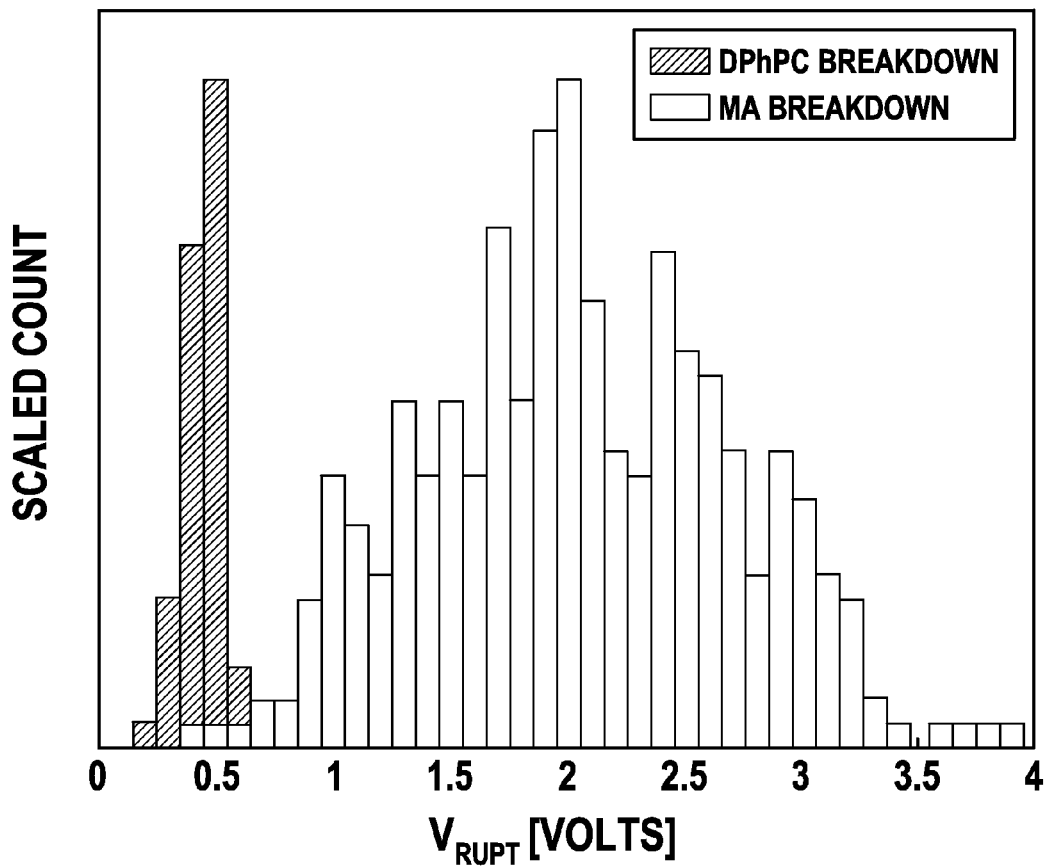
FIG. 3 shows the scaled histograms of rupture voltages of MA membranes (N=330) and DPhPC membranes (N=205) and includes data from several different ~20 μm apertures. MA membranes were confirmed via insertion of MspA proteins.

To determine the rupture voltage of MA and DPhPC membranes, the applied voltage was ramped at about 100 mV/s until the current across the membrane increased abruptly at the rupture voltage, $V_{rup}$. The membrane was then reformed by application of another air bubble, and the procedure was repeated. The histogram of the rupture voltage is presented in FIG. 3. For MA membranes, an average rupture voltage of $V_{rup\_MA}$=2.0 V with a standard deviation of 0.7 V (N=330) was determined. For comparison DPhPC lipid membranes were formed on the same apertures and with the same operating conditions and found $V_{rup\_DPhPC}$=0.50 V with a standard deviation of 0.09 V (N=209). Because the MA membranes withstood relatively high applied voltages, a B&K Precision® 875b capacitance meter could be used to measure their capacitance. For Teflon® apertures with diameters between 56 µm to 85 µm, the largest on which membranes could still be formed, capacitance values ranging from 0.9 to $2.8 \times 10^{-3}$ F/m² were found, indicating average thicknesses between 7 and 22 nm (dielectric constant $\epsilon_r$=2.3). These thicknesses are consistent with the membrane thickness found in vivo of ~8 nm. Without being bound by theory, the inventors attribute the large range of thickness to several factors including the uncertainty of the actual area of the membrane and the unknown extent of solvent incorporation into the membrane. Immediately after membrane formation, the capacitance rose towards an asymptotic value with a time constant of ~5 minutes. Such increase in capacitance is consistent with bilayer formation observed with DPhPC lipids (Biophys J 10:1127 (1970)).

The lifetimes of MA membranes was examined by monitoring the conductance of membranes formed with MspA nanopores. Membranes were left with 200 mV applied until experiments were terminated after more than 3 days (N=4). This puts a lower bound on the MA membrane lifetime at 3 days, significantly larger than the longest lifetime of 1 day observed with DPhPC membranes.

pH influence on membrane stability. The stability of the membranes in the presence of alkaline and acidic conditions from pH 2 to pH 12 was determined by replacing the 1M KCl pH 8.0-buffer on the cis side with different 1M KCl solutions buffered between pH 2 to pH 12. The solution at pH 8 was buffered with 10 mM HEPES, while the other solutions were buffered with an appropriate mixture of 40 mM $CH_3COOH$, Boric Acid and $K_2HPO_4$. The pH of the various buffers was measured using an Orion perpHecT® log R meter with a Beckman® electrode calibrated in the appropriate pH range.

The MA membranes could be formed and reformed with buffer of pH 2 to pH 9 presented to their cis side. The membranes survived at each pH for at least 20 min. At pH as low as 2 the membrane could be readily reformed and pores inserted successfully. Above pH 9 membrane formation was compromised, but bringing the buffer back to a pH of <7 restored membrane formation and stability. The membrane stability was monitored by measuring the ion current. The presence of a measurable current with 200 mV applied indicated formation of leaks and a significant decrease in bilayer stability.

Example 4

Single MspA Channel Experiments

Preparation of the M1-NNN-MspA nanopore is described in U.S. Provisional Application Ser. No. 61/098,938 and its related PCT application, WO 2010/034018, each of which is incorporated herein by reference in its entirety. See also Proc Natl Acad Sci 105:20647 (2008).

The concentration of M1-NNN-MspA in single channel experiments was 0.04 µg/mL in 0.01% wt/v Genapol® and DI-water; the concentration for multi-channel experiments was 0.4 µg/mL in 0.1% wt/v. From this solution, ~10 µL was added to the 100-200 µL of the cis volume above a MA membrane and then mixed thoroughly. The MA membrane was reformed with the air bubble technique, described above, after which stepwise conductance changes were observed. If a conductance appropriate for a single channel was measured, the protein solution was rapidly perfused in the cis well with the working buffer to avoid the insertion of further channels.

Figure 4:
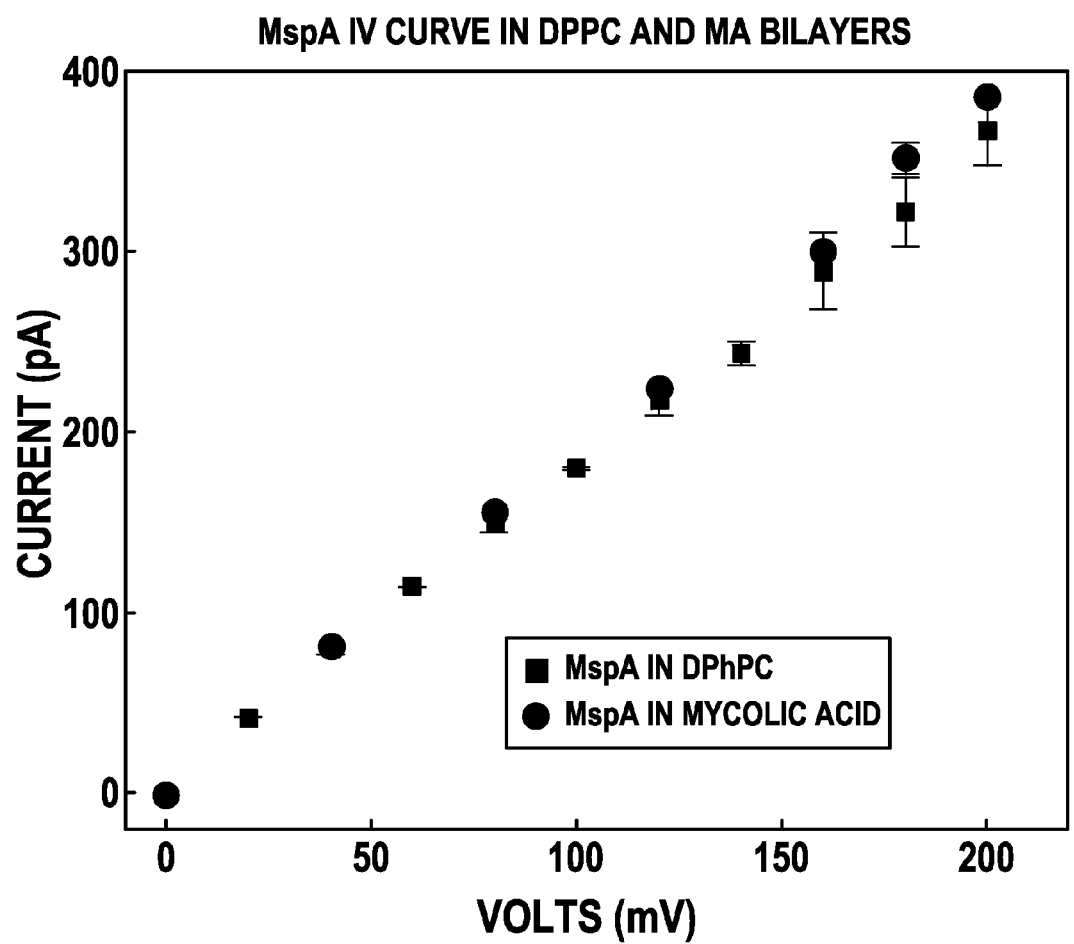
FIG. 4 provides a comparison of MspA I-V curves in MA and DPhPC membranes. At negative voltages MspA gating in both membranes obscures the open state current and is omitted. For MspA in DPhPC membranes N=9 pores, for MspA in MA, N=2.
Figure 5:
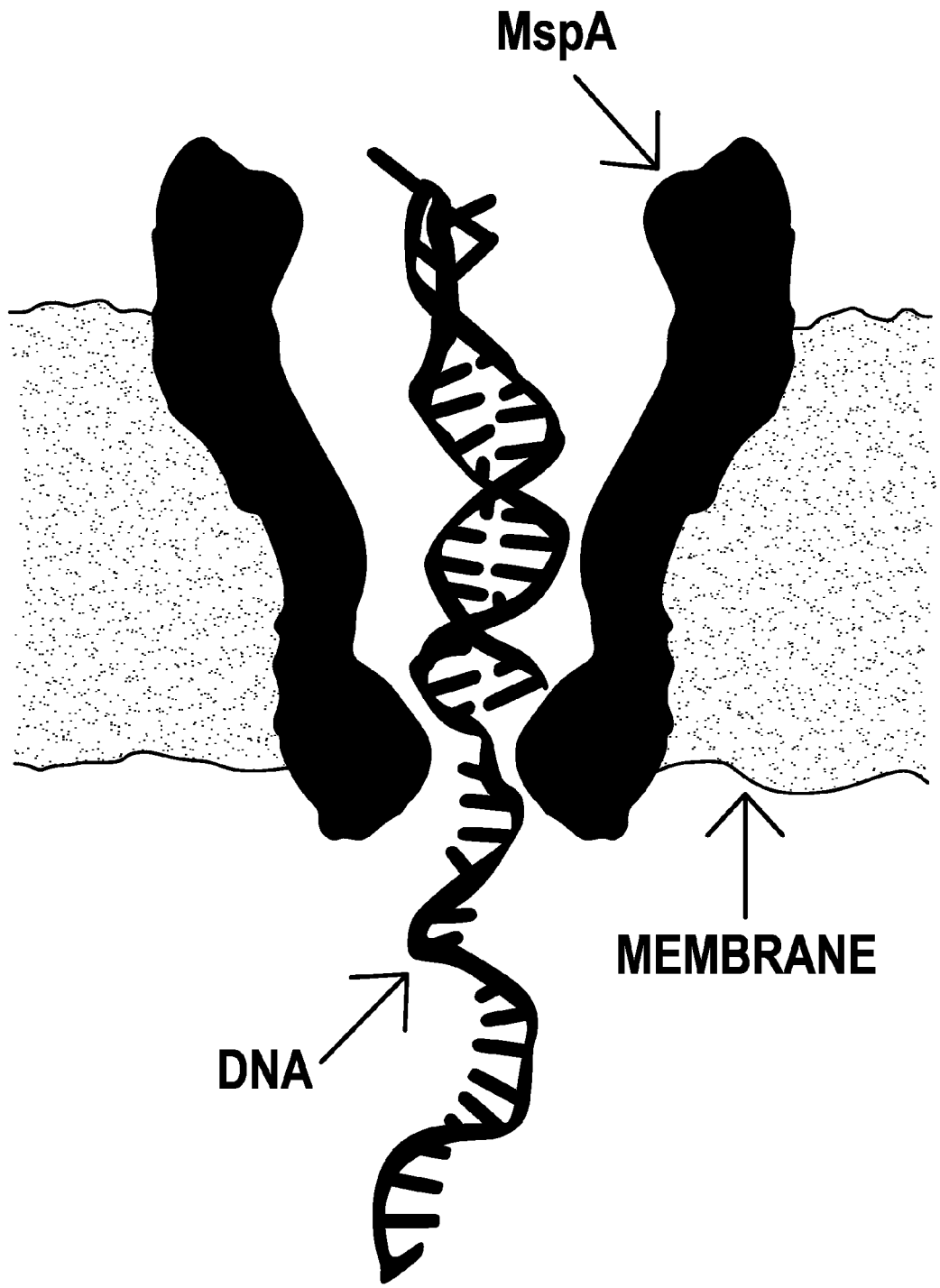
FIG. 5 is a stylized version of MspA in a non-descript membrane; the duplex DNA is unable to thread through the pore's smallest constriction. Image not to scale.
Figure 6:
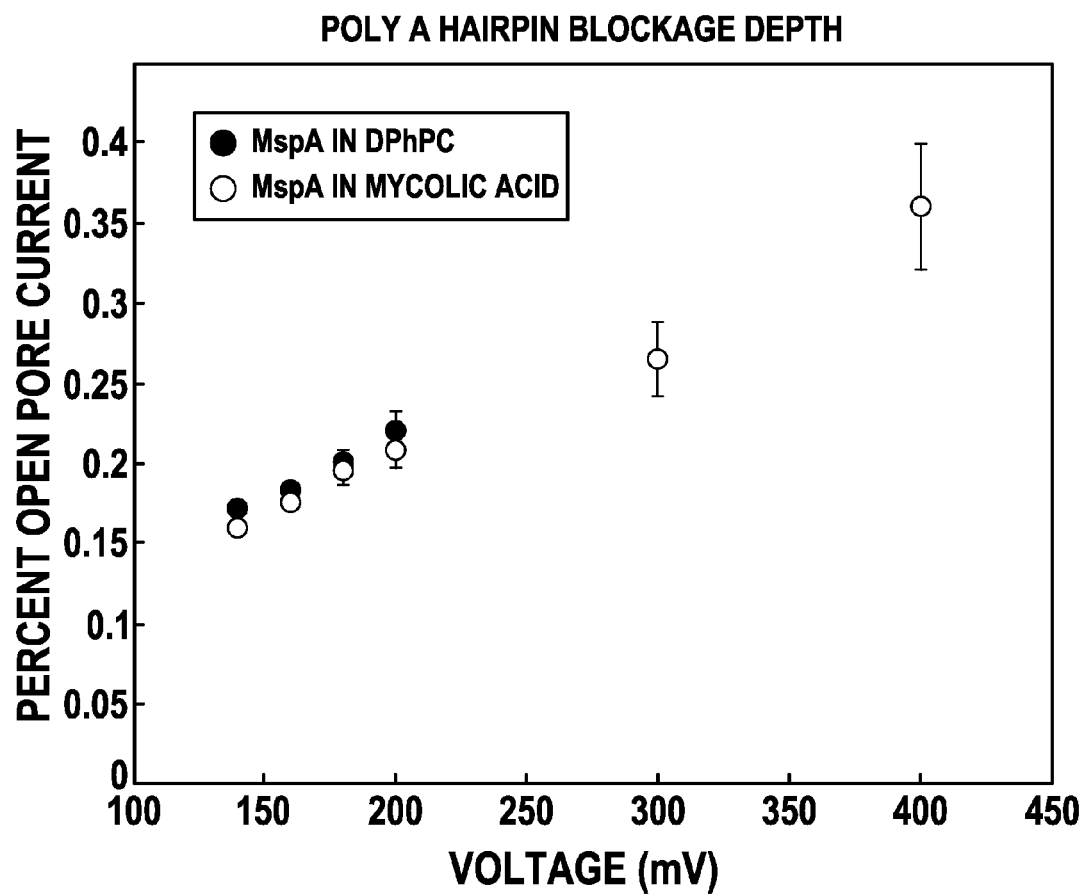
FIG. 6 shows the ion current blockage levels caused by homo-polymer adenine hairpin tails temporarily held in a MspA pore embedded in an MA (red) or DPhPC (blue) membrane. The current is expressed as fraction of the open state current at the given voltage. At voltages above 200 mV DPhPC membranes become too fragile for extended experimentation, while MA membranes allow measurements at much higher voltages. The duration of events recorded above 400 mV were too short to confidently extract a characteristic ion current.

To demonstrate that the MspA incorporated in MA were proper trans-membrane channels their I-V curves were measured and DNA translocation experiments were conducted. The I-V curves of MspA exhibit the same quantitative characteristics as those of MspA in DPhPC membranes (FIG. 4) indicating that MspA is able to span the membrane and that the inner channel of MspA was not appreciably affected by its membrane environment. In order to further insure the channel integrity and the usefulness of the MA-MspA combination for nanopore sequencing, DNA translocation experiments were conducted. Experiments were repeated that had been previously carried out with single MspA channels in DPhPC membranes (Proc Natl Acad Sci 107:16060 (2010)). Since single-stranded DNA translocates too rapidly (>1 nt/µs) to observe well-characterized current signatures, a DNA hairpin was used that could not complete translocation until the double stranded section dissociated. During this brief pause the single stranded section of the hairpin DNA held in MspA's constriction yielded well-resolved ion current levels. These current levels were characteristic of the nucleotides residing at the constriction (FIG. 5). Experiments were carried out with several DNA hairpin tail sequences and it was determined that the ion current levels to be indistinguishable from analog experiments with MspA in DPhPC membranes (FIG. 6).

Example 5

Summary and Commentary on Results of Experiments 1-4

MA membranes exhibit more stability than comparable DPhPC membranes. The foregoing experiments demonstrate the first unsupported membrane established in vitro made from MA. In comparison with DPhPC membranes, the MA membranes withstand considerably larger voltages before rupturing. Experimentally, it is known that a number of factors influence the stability of membranes. The MA and DPhPC membranes have significantly different melting temperatures; *M. tuberculosis* cell wall extracts have been found to change phase as high as 63° C., while DPhPC has no known phase change. It was concluded that the remarkable robustness of MA membranes is attributed to the structure and interactions of MA's constituent lipid chains.

The significant differences between MA and DPhPC molecules are the chemical structures of the lipid headgroups and tails. For example, studies have been performed regarding the importance of the lipid chain length. While the negatively charged MA headgroup is substantially different than the zwitterionic DPhPC headgroup, neither form hydrogen bonds at pH 8, suggesting that the headgroup is unlikely to account for the rupture voltage differences. Thus, without being bound by theory, the inventors postulate that the size and configuration of the MA tails and associated thickness of the resulting membranes appear to be the determinant cause of the stability of the MA membranes. In particular, it has been suggested that the assembly of MA lipid tails within the membranes may play a significant role in the membrane's function in vivo (Trends Microbio 18:109 (2010)). Artificial MA membranes are useful for the closer examination of the Mycobacterial outer membrane.

Trans-membrane pores in MA membranes. The influence of the membrane on pore formation, conformation and function is an unanswered question of interest in drug development and in understanding the folding mechanics of porins. For the channel MspA in MA and in DPhPC membranes it was observed that the open-channel current exhibits identical conductance and rectification. Furthermore identical DNA translocation properties through MspA were observed in the two membranes. These conductance and DNA translocation properties are highly sensitive to the structure of MspA (Proc Natl Acad Sci 107:16060 (2010)). Hence, these observations suggest that the substantial difference between membranes composed of MA and DPhPC does not appreciably alter the trans-membrane conformation and function of MspA channels.

While illustrative embodiments have been illustrated and described, it will be appreciated that various changes can be made therein without departing from the spirit and scope of the invention.

The embodiments of the invention in which an exclusive property or privilege is claimed are defined as follows:

1. An artificial bilayer membrane spanning the opening of an aperture, the membrane comprising a mycolic acid and having a rupture voltage greater than 0.5 V.

2. The membrane of claim 1, wherein the mycolic acid is a crosslinked mycolic acid.

3. The membrane of claim 1 further comprising a nanopore.

4. The membrane of claim 3, wherein the nanopore is a protein pore.

5. The membrane of claim 3, wherein the nanopore is α-hemolysin or a variant thereof, a *Mycobacterium smegmatis* porin (Msp) or a variant thereof, or OmpATb.

6. The membrane of claim 3, wherein the nanopore is a mutant MspA porin.

7. The membrane of claim 6, wherein amino acids at positions 90, 91, and 93 of the mutant MspA porin are each substituted with asparagine.

8. The membrane of claim 1, wherein the membrane is an unsupported membrane.

9. The membrane of claim 1, wherein the membrane has a rupture voltage of at least about 1.0 V.

10. A system comprising an artificial bilayer membrane positioned between a first liquid conductive medium and a second liquid conductive medium, wherein the artificial membrane comprises a mycolic acid and has a rupture voltage greater than 0.5 V.

11. The system of claim 10, wherein the membrane further comprises a nanopore.

12. The system of claim 11, wherein at least one liquid conductive medium comprises an analyte.

13. The system of claim 12, wherein the analyte is a nucleic acid or a protein.

14. The system of claim 11, wherein the nanopore is α-hemolysin or a variant thereof, a *Mycobacterium smegmatis* porin (Msp) or a variant thereof, or OmpATb.

15. The system of claim 11, wherein the nanopore is a mutant MspA.

16. A method for detecting an analyte comprising:
(a) providing a system comprising the artificial bilayer membrane of claim 1, wherein the artificial bilayer membrane is positioned between a first liquid conductive medium and a second liquid conductive medium, and wherein the membrane comprises a nanopore;
(b) applying an electric field to the system sufficient to electrophoretically translocate an analyte through the nanopore; and
(c) measuring an ion current as the analyte interacts with the nanopore to provide a current pattern.

17. The method of claim 16, further comprising identifying the analyte.

18. The method of claim 17, wherein identifying the analyte comprises comparing the current pattern to a known current pattern of a known analyte.

19. An artificial bilayer membrane spanning the opening of an aperture, wherein the membrane comprises a mycolic acid and can resist electroporation at an applied 200 mV for more than 24 hours.

* * * * *